United States Patent
Grayzel et al.

(10) Patent No.: US 9,238,124 B2
(45) Date of Patent: *Jan. 19, 2016

(54) MEDICAL GUIDE ELEMENT WITH DIAMETER TRANSITION

(71) Applicants: Jeffrey Grayzel, Morristown, NJ (US); Joseph Grayzel, Englewood, NJ (US)

(72) Inventors: Jeffrey Grayzel, Morristown, NJ (US); Joseph Grayzel, Englewood, NJ (US)

(*) Notice: Subject to any disclaimer, the term of this patent is extended or adjusted under 35 U.S.C. 154(b) by 216 days.

This patent is subject to a terminal disclaimer.

(21) Appl. No.: 13/918,906

(22) Filed: Jun. 15, 2013

(65) Prior Publication Data
US 2014/0163471 A1    Jun. 12, 2014

Related U.S. Application Data

(63) Continuation of application No. 12/233,272, filed on Sep. 18, 2008, now Pat. No. 8,485,969.

(51) Int. Cl.
*A61B 1/00*    (2006.01)
*A61M 25/09*   (2006.01)
*A61M 29/00*   (2006.01)

(52) U.S. Cl.
CPC .............. *A61M 25/09* (2013.01); *A61M 29/00* (2013.01); *A61M 2025/09083* (2013.01); *A61M 2025/09125* (2013.01); *A61M 2025/09175* (2013.01)

(58) Field of Classification Search
CPC ................... A61M 25/09; A61M 2025/09175; A61M 2025/09083; A61M 29/00; A61M 25/104; A61M 2025/0681; A61M 2025/09091; A61M 25/0662; A61M 2025/09125
See application file for complete search history.

(56) References Cited

U.S. PATENT DOCUMENTS

| | | |
|---|---|---|
| 4,345,602 A | 8/1982 | Yoshimura |
| 4,650,472 A | 3/1987 | Bates |
| 4,925,445 A | 5/1990 | Sakamoto |
| 5,002,559 A | 3/1991 | Tower |
| 5,035,686 A | 7/1991 | Crittenden |
| 5,059,183 A | 10/1991 | Semrad |
| RE33,911 E | 5/1992 | Samson |

(Continued)

FOREIGN PATENT DOCUMENTS

JP    06178812    6/1994

OTHER PUBLICATIONS

English machine translation for JP 06178812 (Okada) Jun. 29, 1994.*

*Primary Examiner* — Katherine M Shi

(57) ABSTRACT

Improved medical filaments for use with dilators to be inserted into a patient, for example into the vascular lumen, are provided, as well as combinations of filaments and dilators. Methods for use of such filaments and filament-dilator combinations are also described. The filament includes a proximal segment and a distal segment. The diameter of the distal segment is greater than the diameter of the proximal segment. The change in diameter is abrupt, providing a discrete step transition at a point along the filament which presents a proximally-facing surface on the distal segment. When the proximal segment of the filament is fully inserted into a dilator having a distal tip adapted for insertion into a patient, the dilator distal tip firmly abuts the proximally-facing end surface of the distal segment. The relative dimensions of the dilator tip and the discrete stepped transition of the filament provides full shielding or over shielding of the dilator tip, thereby facilitating passage of the dilator tip along the tissue track, through the puncture hole and into the orifice.

52 Claims, 13 Drawing Sheets

(56) References Cited

U.S. PATENT DOCUMENTS

| | | |
|---|---|---|
| 5,122,136 A | 6/1992 | Guglielmi |
| 5,141,494 A | 8/1992 | Danforth |
| 5,147,317 A | 9/1992 | Shank |
| 5,174,302 A | 12/1992 | Palmer |
| 5,192,295 A | 3/1993 | Danforth |
| 5,230,348 A | 7/1993 | Ishibe |
| 5,256,145 A | 10/1993 | Atkinson |
| 5,303,714 A | 4/1994 | Abele |
| 5,312,328 A | 5/1994 | Nita |
| 5,312,340 A | 5/1994 | Keith |
| 5,312,415 A | 5/1994 | Palermo |
| 5,318,527 A | 6/1994 | Hyde |
| 5,341,818 A | 8/1994 | Abrams |
| 5,345,945 A | 9/1994 | Hodgson |
| 5,353,808 A | 10/1994 | Viera |
| 5,385,152 A | 1/1995 | Abele |
| 5,465,733 A | 11/1995 | Hinohara |
| 5,484,409 A | 1/1996 | Atkinson |
| 5,527,298 A | 6/1996 | Vance |
| 5,695,111 A | 12/1997 | Nanis |
| 5,724,989 A | 3/1998 | Dobson |
| 5,830,155 A | 11/1998 | Frechette |
| 5,891,082 A | 4/1999 | Leone |
| 5,957,903 A | 9/1999 | Mirzaee |
| 6,042,876 A | 3/2000 | Deem |
| 6,090,130 A | 7/2000 | Nash |
| 6,390,992 B1 | 5/2002 | Morris |
| 6,390,993 B1 | 5/2002 | Cornish |
| 6,612,998 B2 | 9/2003 | Gosiengfiao |
| 6,613,002 B1 | 9/2003 | Clark |
| 6,675,033 B1 | 1/2004 | Lardo |
| 6,726,700 B1 | 4/2004 | Levine |
| 6,751,660 B1 | 6/2004 | Mansingh |
| 6,837,898 B2 | 1/2005 | Boyle |
| 7,192,433 B2 | 3/2007 | Osypka |
| 2002/0055714 A1 | 5/2002 | Rothschild |
| 2004/0167439 A1 | 8/2004 | Sharrow |
| 2004/0167440 A1 | 8/2004 | Sharrow |
| 2008/0027380 A1 | 1/2008 | Wholey |
| 2008/0033481 A1 | 2/2008 | Gilson |
| 2009/0112126 A1 | 4/2009 | Keating |

\* cited by examiner

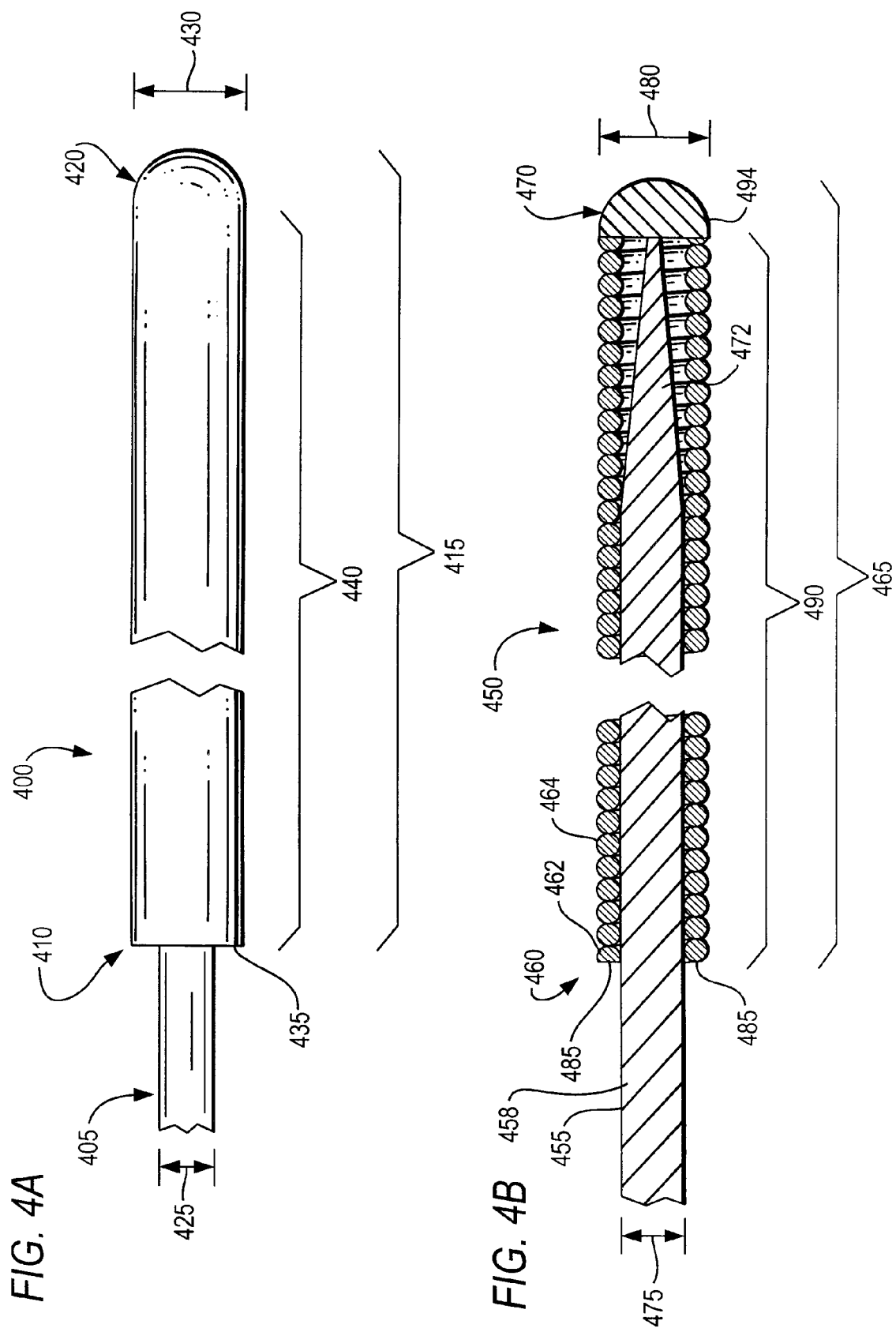

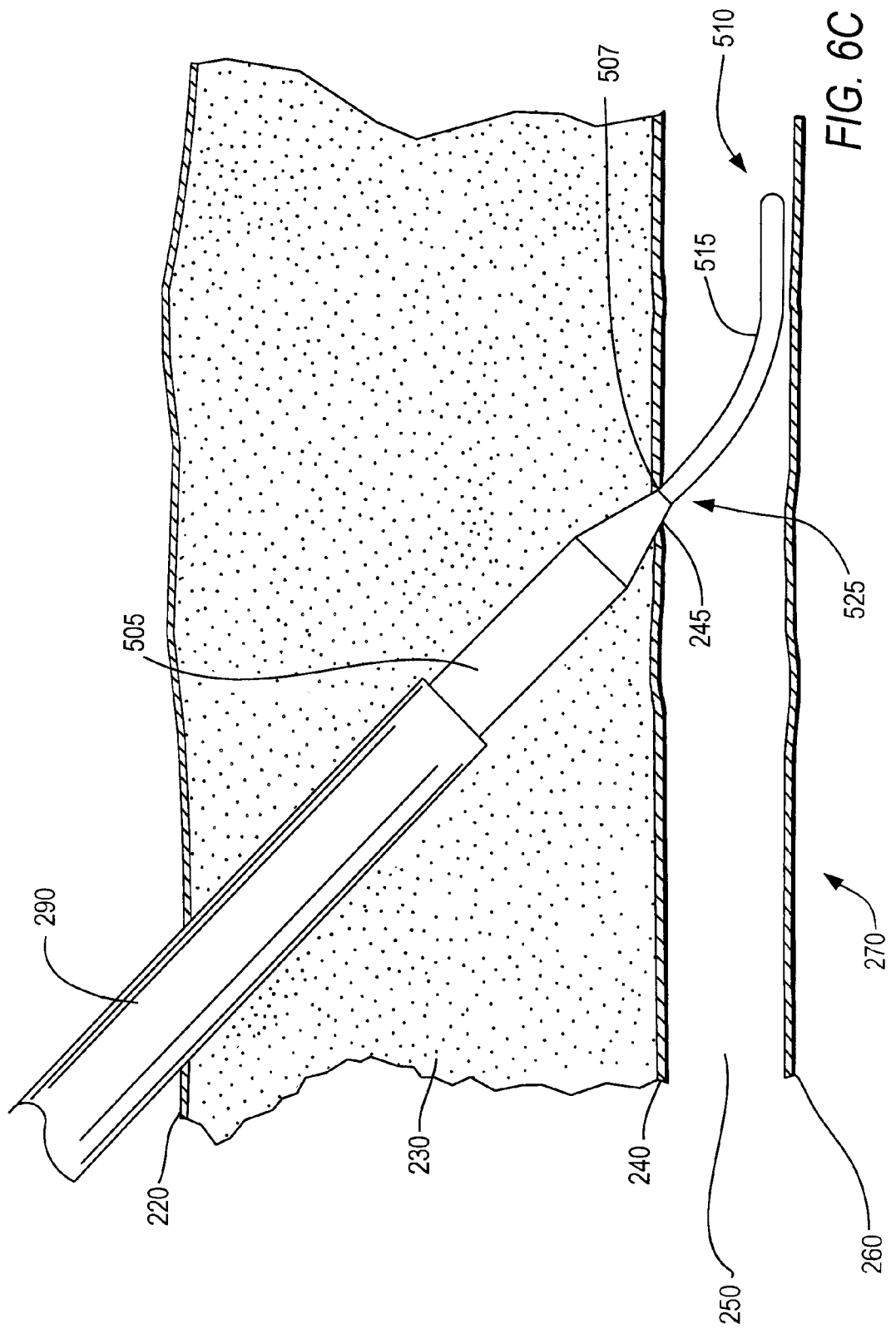

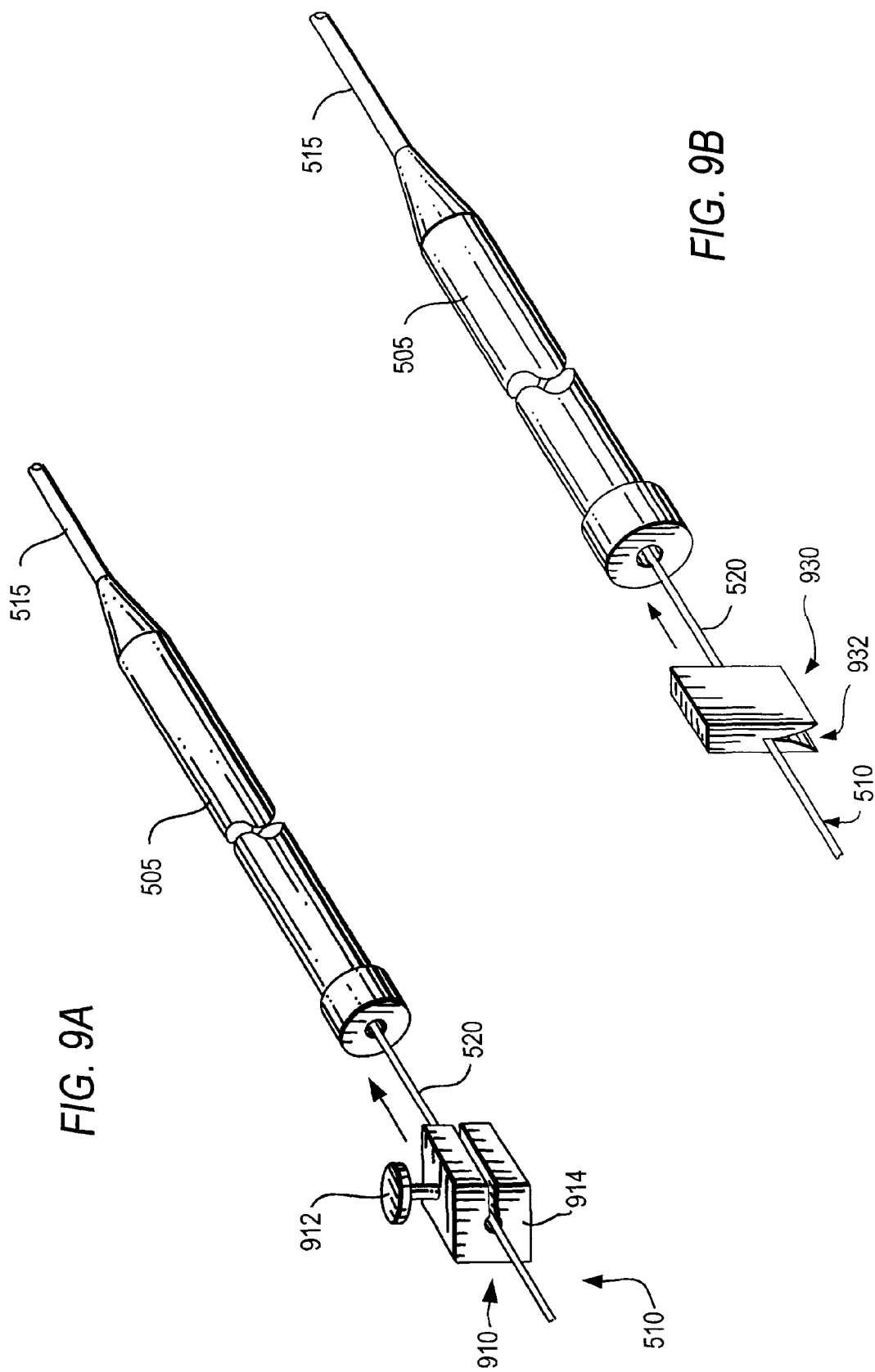

MEDICAL GUIDE ELEMENT WITH DIAMETER TRANSITION

This application is a continuation of and claims the benefit of U.S. patent application Ser. No. 12/233,272 filed Sep. 18, 2008, which is hereby incorporated by reference in its entirety.

FIELD OF THE INVENTION

The invention generally relates to apparatus and methods for inserting catheters into the human body employing percutaneous techniques for vascular access. More particularly, the invention relates to a novel introducing guide element and to novel combinations of said introducing guide element with a matching dilating catheter.

BACKGROUND

In present medical practice, insertion of catheters into blood vessels and other body structures is most often accomplished by the percutaneous technique. The Percutaneous Technique is a term of art for a transcutaneous method that avoids surgical cut-down and dissection. Instead, a hollow-bore needle is employed to penetrate the skin or surface, traverse the subcutaneous tissue and other intervening structures, and enter the lumen of the blood vessel or body structure. Then a tracer or flexible filament, typically in the form of a metallic guidewire, is inserted through the bore of the needle so that it enters the vascular lumen and extends into the lumen to a distance sufficient to prevent accidental or inadvertent dislodgement. The flexibility of the guidewire reduces the likelihood of injury to the interior surface of the blood vessel within which it is advanced and manipulated to ensure a secure position. After the guidewire has been inserted into the vascular lumen, the practitioner, holding the proximal segment of the guidewire, i.e. the segment residing outside of the human body and above the skin, carefully withdraws the needle. Once the needle is entirely outside the body, it is slidably withdrawn from the guidewire and set aside. The guidewire now constitutes a smooth rail for slideable insertion of other devices, such as catheters of various types. This concept and method was innovated by Ivan Seldinger in 1953 and is often referred to as the "Seldinger technique".

Building upon the original Seldinger technique for percutaneous access, Drs. Donald Desilets and Richard Hoffman in 1965 innovated the combination of a dilating catheter and a separate, thin-walled tubular conduit, a sheath, carried thereon to gain access to the vascular lumen via the guidewire. As detailed below, a dilating catheter with a conically tapered tip is advanced over and along the guidewire and dilates the arteriotomy puncture created by the needle up to the selected diameter of the chosen catheter. The main body of the dilating catheter carries a thin-walled sheath into the blood vessel. Further advancement of this catheter-sheath combination introduces the sheath into the blood vessel to a secure indwelling position, whereupon the guidewire and the dilating catheter are removed, leaving the sheath in place to provide a clear cylindrical path from skin into the vascular lumen. In this manner, the sheath provides a smooth unobstructed passageway for the insertion of diagnostic and/or therapeutic catheters and devices into the vascular system.

This procedure is referred to as the "Desilets-Hoffman technique" and is also referred to as the "modified Seldinger technique" or "Seldinger-Desilets-Hoffman technique", or simply "SDH technique" as will be referred to herein. This technique can be applied to access blood vessels as well as other anatomic structures.

DEFINITIONS

As used herein, the term "percutaneous technique" refers to a transcutaneous method that generally avoids surgical cut-down and dissection.

The term "guide element", "guiding filament", or simply "filament" refers to an elongate, flexible member, often metal, such as an introducing guidewire, as is well known in the art.

The term "distal" refers to a relative position or direction away from the practitioner and closer to or towards the patient. When used in reference to a guidewire, the distal end refers to the end of the guidewire inserted into the patient.

The term "proximal" is used to refer to a relative position or direction close to or towards the practitioner and away from the patient. When used in reference to a guidewire, the proximal end refers to the end closest to and held by the operator.

The terms "dilating catheter" and "dilator" refer to a catheter for use in the SDH technique, which enlarges the tissue track and target orifice to a desired size.

The "target orifice" or "target opening" or "opening" is the hole in the blood vessel or the hole in another anatomic structure that is to be dilated by the dilator. When in the artery it is termed an arteriotomy.

The term "match" or "matching" as used to describe the needle, the guidewire and the dilator of the prior art means that the guidewire is of a diameter, as known in the art, close to but smaller than the bore of the hollow needle so that it can pass through the bore of the hollow needle and yet substantially block the backflow of blood from the opening and through the needle; and that the hollow bore of the dilator is of a diameter, as is known in the art, close to but larger than the diameter of the guidewire so that it can pass smoothly over the guidewire.

The Desilets-Hoffman Technique and the Present Art

Vascular access procedures, as currently practiced according to the SDH technique, employ four elements or devices: (1) a hollow-bore needle to puncture the blood vessel; (2) a short guidewire which may be referred to as an introducing guidewire; (3) a dilator with a cylindrical main body, a hollow bore, a conically-tapered distal portion, and a distal tip having an inner diameter matched to the outer diameter of the guidewire; and (4) a cylindrical, thin-walled, tubular sheath which sits snugly on the main body of the dilator such that upon dilation of the arteriotomy by the dilator and entry therein, the main body of the dilator supports and carries the thin-walled sheath into the blood vessel.

As described above, the needle is used to puncture the wall of the blood vessel or body structure; when in the artery this creates the arteriotomy. Due to the difference between the outer diameter of the needle and the outer diameter of the guidewire, there can be a gap between the perimeter of the puncture created by the needle's outer edge and the guidewire extending through the puncture. This gap is minimized by an optimum match of the guidewire to the needle's internal diameter. An elastic vessel may elastically contract around the guidewire to reduce or eliminate the gap, while a less elastic vessel may retain its original dimension leaving a larger gap. If any gap exists, blood may flow out of the vessel. This backflow of blood can cause bleeding, a hematoma, pseudo-aneurysm, or other complications. The larger the gap the more backflow will occur Contemporary practice of the SDH method for percutaneous entry employs a short introducing guidewire that is cylindrical and of uniform diameter along its entire length. The usual prior-art guidewire consists of two principal parts: a cylindrical, longitudinal inner "core-wire" around which a second wire, called a "coil-wire", is helically or spirally wound with a tight pitch so that successive turns abut each other, leaving little or no space between each turn so as to create a surface that is as smooth and regular as possible. To prevent this helical coil from unraveling it is usually bonded by solder or other means to the core-wire at several points along its length, and most importantly, at the very distal tip of the assembly. Often, the core-wire has a tapered end toward its distal tip, the taper providing increased flexibility of the core wire over the distal few centimeters of length, and therefore increased flexibility of the distal end portion of the wire assembly. The constant outer diameter along the entire length of the guidewire ensures a good, unvarying fit with the internal diameter of the tip of the dilator as it is advanced over the guidewire. Additionally, the guidewire may have a curved distal end portion, referred to as a J-tip, whose length may vary from 2 cm to 5 cm or greater depending on the construction of the specific wire. The J-tip maintains the guidewire within the main lumen of the major vessel and prevents its distal tip from being diverted into a side-branch. Also, the J-tip reduces the possibility of trauma or vessel perforation because it has a curled end instead of a discrete tip.

A conventional dilator has a hollow, cylindrical body, often with a hub at its proximal end, and a tapered portion at its distal end, which tapers from the cylindrical body down to the distal tip, i.e. the outer diameter at the cylindrical portion is larger than the outer diameter at the tip. FIG. 1A shows a prior-art assembly of a guidewire 110 inserted through a typical dilator 120 having a distal end 130 comprised of a distal tapered portion 132, a distal tip 134 having an outer diameter OD2 and a distal tip opening having an inner diameter ID1. The dilator 120 has a cylindrical body 140 and an inner passageway 142. The outer diameter along the cylindrical body portion of the dilator 120 is represented by OD3 which is greater than OD2, the tapered portion 132 accounting for this diameter change.

Guidewire 110, comprising core wire 111 and coil wire 112, has an outer diameter OD1 and is dimensioned such that OD1 is matched to, but slightly less than, the inner diameter of the bore of the needle. The inner diameter ID1 of the opening at the distal tip 134 is matched to the guidewire's outer diameter OD1, taking account of the need for some clearance to eliminate sliding frictional forces and allowance for the manufacturing tolerances or other variations from the nominal diameters of each component. It should also be noted that for manufacturing reasons, the extrusion creating the body of the dilator may sometimes be fabricated with a bore larger than that required to appropriately match the guidewire, in which case the dilator undergoes a secondary operation which reduces the diameter of the opening at its most distal portion to match the outer diameter of the guidewire with which it will mate.

The cylindrical body of the dilator has an outer diameter, measured in French units (3-French units=1.0 mm), corresponding to the diagnostic or therapeutic catheter to be used later in the procedure. The distal-tip region of all dilators, regardless of the diameter of the main body, tapers down toward its tip and approaches the outer diameter of the guidewire as closely as possible. However, the dilator's leading tip must have sufficient wall thickness to maintain its structural integrity as it passes through tissue. Being fabricated of a flexible plastic such as polyethylene, polypropylene, polyurethane, or the like, the tip cannot be formed with too thin a wall at the very distal tip, as an unduly thin wall will become frayed or deformed as it forcibly progresses through the skin, subcutaneous tissue, and vascular wall. For example, a muscular artery, such as the femoral artery, strongly resists passage of the distal tip of the dilator. Hence, there must be a pronounced difference between the inner and outer diameters of the tip of the dilator thereby creating a wall thickness at the tip of sufficient substance to maintain the integrity of the tip while it withstands the forces it encounters during passage, and to prevent it from fraying or deforming. As a result, the tip of the dilator must present a relatively annular, forward-facing tip, causing a step-up or discrete increase in diameter at the transition to the dilator tip. During insertion into a blood vessel this diameter transition creates a discontinuity. It engages the outer wall of the blood vessel and must enter through the smaller hole created by the puncturing needle, through which the guidewire now resides. FIG. 1A illustrates the diameter transition or discontinuity from the guidewire 110 to the distal tip 134 of the dilator 120 of the prior-art. Currently available materials only allow for the wall thickness to be reduced to a certain level, below which level the tip has insufficient strength and integrity.

FIG. 1B illustrates a prior-art assembly including a deformed dilator 160 shown over guidewire 110. The distal tip 174 of dilator 160 has a crushed portion 184, as well as a flared portion 194. The tip of a dilator may suffer many different types of deformation and may have torn, buckled, crushed, flared and spindled regions. Such fraying causes additional resistance to passage of the dilator through a tissue track and into the puncture in a vessel wall because the frayed portion presents more surface area to catch on the edges of the tissue track and the puncture. In many instances, such fraying causes additional damage, even more tearing at the arteriotomy. The frayed dilator tears the artery to a greater extent than the discontinuity alone, as well as being more uncontrolled, as described above, and further exacerbates the complications noted above.

A numerical example will illustrate the foregoing description of a needle, guidewire, and dilator of the prior art, and the manner in which the dilator tip engages the puncture hole in the vessel wall. The SDH technique for percutaneous entry into the femoral artery commonly employs an 18-gauge thin-wall needle for arterial puncture, through which is inserted a close-fitting introducing guidewire with outer diameter ("OD") of 0.038-inch. The main body of the dilator is frequently 6-French (~0.079-inch outer diameter) for many procedures, but is most often in the range of 4-8 French but may be larger. For children, the outer diameter may be as small as 2-French, and possibly less for neonates. For the present we will use the example of a 6-French dilator. From the main cylindrical outer body of the dilator, a short distal portion tapers conically down toward the outer diameter of the guidewire. However, the physical properties of flexible plastics together with limitations in manufacturing methods limit how thin a wall can be achieved at the distal tip, resulting in a wall thickness of 0.010-inch at the very distal tip of the dilator. To slide and advance freely over the guidewire with a 0.038-inch outer diameter, the diameter of the opening at the tip of a 6-French dilator is approximately 0.040-inch, the difference allowing for manufacturing tolerances and variation of both the guidewire and dilator, and to avoid sliding friction between dilator and guidewire. Therefore, the dilator tip with an opening having an inner diameter of 0.040-inch and wall thickness of 0.010-inch at its distal tip will have an outer diameter of 0.060-inch, which is 58% greater than the 0.038-inch outer diameter of the guidewire. This represents a substantial relative increase in dimension, presenting an abrupt step which enters the femoral arteriotomy by blunt force as this step-up in diameter engages and presses against the arterial wall. The entire blunt-step profile of the dilator tip surrounding the guidewire enters the puncture hole at one instant as the arteriotomy tears open to accept the full diameter of the dilator tip. There is nothing to shield the perimeter of the puncture hole from being assaulted with a dilator tip that is too large to be accepted into the existing orifice. Often, the required force is considerable and the dilator tip generally "pops" through the puncture hole suddenly with a palpable abruptness. As this dilator tip penetrates the arteriotomy with brute force it traumatizes and tears the arterial wall. This same problem also occurs during other medical procedures when a dilator enters an opening that is smaller than its distal tip outer diameter.

In the numerical example described above, the inner diameter of the opening at the dilator tip was 0.040-inch. This is the inner diameter at the tip area, but the bore diameter in the main body of the dilator may be equal to or larger than 0.040-inch. During the manufacturing process when the tapered conical tip is created on the dilator, the opening at the tip is reduced to the specified diameter, in this case 0.040-inch, at this same time.

Referring now to FIGS. 2A-2C, the SDH Technique of the percutaneous procedure is performed in the following manner. As shown in FIG. 2A, a needle 205, having hub 206 and tip 207 penetrates the skin 220, traverses the subcutaneous tissue 230 and other soft intervening structures, creating the initial tissue track, and punctures the vessel wall 240. Its tip 207 enters the lumen 250 of blood vessel 270 creating puncture hole 245. A guidewire 110 is inserted through the hollow bore of needle 205 and into the vessel lumen 250. Once the guidewire 110 is securely in place, the needle 205 is removed, leaving guidewire 110 in place extending from outside skin 220 to inside lumen 250. Blood may flow out of the puncture 245 in vessel wall 240 but the presence of guidewire 110 in the puncture hole tends to minimize the leakage of blood.

A dilator 280 carrying a sheath 290 is then advanced over the guidewire 110, through skin 220 and subcutaneous tissue 230 along the tissue track to the wall 240 of blood vessel 270. FIG. 2B shows an enlarged view of the distal end of the dilator 280 approaching the puncture hole 245, previously created by the needle, in wall 240. As can be appreciated by the skilled artisan, the significant difference in diameter between the outer diameter of the guidewire OD1 and the outer diameter OD2 of the dilator's distal tip 284 causes resistance to further advancement of the dilator, resulting in trauma to the vessel wall 240 as the dilator's distal tip 284 penetrates the vessel wall 240 through the smaller puncture hole 245, particularly when the arterial wall of the puncture hole is snugly fitting around the guidewire 110.

The difference in diameter from guidewire 110 to distal tip 284 of the dilator 280 necessitates that additional force be exerted by the practitioner to advance tip 284 along the tissue track through one or more of skin 220, tissue 230 and vessel wall 240. The blunt end of tip 284 effectively focuses the force applied by the practitioner to displace or tear through the several layers. As shown in FIG. 2C, the bluntness of tip 284 meets substantial resistance to its entry into the puncture hole 245 in wall 240 of the blood vessel, particularly in muscular arteries. The enlarged view within FIG. 2C shows the deformation of the vessel wall by the dilator tip 284 as it attempts to enter the smaller diameter puncture hole 245, through which the guidewire 110 extends. Therefore, the practitioner must increase the force he exerts on the dilator in order to overcome this resistance. The vessel wall finally yields, traumatically, by tearing and accepts the full diameter of tip 284. The practitioner feels a palpable "pop" sensation as the vessel wall tears around the puncture hole 245. In addition, upon penetrating vessel wall 240, the sudden reduction in resistance frequently causes the dilator to lurch forward, pushing dilator 280 uncontrollably into the lumen 250, and may result in distal tip 284 of dilator 280 striking opposite wall 260 of vessel 270 and causing a damaging abrasion. Similar resistance is encountered in other medical procedures when a dilator is advanced to and through an opening in an anatomic structure that is smaller than the outer diameter of the distal tip of the dilator.

In the percutaneous technique, the dilator 280 carries sheath 290. The dilator-sheath assembly is then advanced through the vascular wall 240 until the sheath's distal portion resides in the vessel lumen 250. The dilator and guidewire are then removed, leaving a channel of the desired French-size into the vessel via the thin-walled sheath. The operator/surgeon is now able to insert via the sheath a diagnostic or therapeutic catheter, or other devices.

FIG. 3A is a top view of blood vessel 270 after it has been punctured by a beveled needle of the prior art, illustrating the typical curvilinear-shaped slit of puncture 310 in vessel wall 240 created by beveled tip 207 of needle 205. The angle of the bevel, the orientation of the bevel as it engages vessel wall 240, and the angle at which the needle approaches vessel wall 240, create a curvilinear-shaped slit puncture 310, not a circular-shaped puncture.

FIG. 3B is a top view of vessel 270 after it has been punctured by a beveled needle and dilated by dilator 280 of the prior art. After needle 205 creates an initial puncture, guidewire 110 is inserted through the bore of needle 205 and into lumen 250 of vessel 270. Needle 205 is slidably removed keeping guidewire 110 in place. Dilator 280 is advanced over guidewire 110 to vessel 270. When distal tip 284 of dilator 280 reaches vessel wall 240, at least a portion of tip 284 impacts vessel wall 240 causing the wall to deform. When the deformation of vessel wall 240 reaches its elastic limit, the wall tears, causing a palpable "pop" sensation. The tearing may occur in one or more places along puncture 320 but generally occurs at the ends of the puncture, as shown by torn regions 330 and 340. As a result of the tearing and dilation, puncture 320 is much wider than the original puncture 310 and more irregular.

The tearing caused by dilator 280 is worse if tip 284 frays or is otherwise deformed before reaching vessel wall 240. As the exposed tip 284 of the dilator is advanced through the tissue track, the resistance of tissue 230 often causes tip 284 to fray or to be otherwise deformed.

FIG. 3C is a top view of blood vessel 270 after it has been punctured by a beveled needle and dilated by prior-art dilator 160 having a frayed distal tip 174. An initial, curvilinear puncture 310 is created by needle 205. Guidewire 110 is then deployed into lumen 250 of blood vessel 270. As dilator 160 passes through skin 220 and subcutaneous tissue 230, tip 174 of dilator 160 deforms and frays in a similar fashion as depicted previously at tip 184 and tip 194. When frayed tip 174 reaches vessel wall 240, it presents a more irregular surface against vessel wall 240 than would an unfrayed tip, and the operator feels increased resistance compared to an unfrayed tip. Vessel wall 240 deforms as frayed distal tip 174 is advanced, and finally vessel wall 240 tears in an uncontrolled manner. The resulting tearing is more pronounced and varied than that caused by the unfrayed dilator tip 130, as shown at torn regions 360, 370 and 380. Torn regions 360 and 380 at the ends of puncture 350 are more extensive than torn regions 330 and 340. As a result of the extensive tearing and dilation, puncture 350 is larger than puncture 320 and much larger than needle puncture 310.

The tearing of the vessel wall and trauma caused to the surrounding areas by the deformed or frayed tip of the dilator are significant problems for the patient. Such damage results in more lengthy and difficult hemostasis at the conclusion of the invasive procedure. Also, a hematoma and other complications are more likely to occur.

As illustrated above, there are deficiencies with the current tools used for the percutaneous technique, particularly the SDH technique. One problem is caused by the discrete step-like increase in diameter from guidewire to dilator tip. This increase in diameter is a principal factor determining the force which must be exerted by the dilator tip on tissue during passage along the tissue track and causes the resistance to entry of the dilator tip into the arteriotomy in the muscular wall of the blood vessel. The operator experiences this noticeable resistance as the blunt leading face of the dilator tip tries to pass through the arteriotomy which is too small to easily accept it.

Another problem encountered in the prior art is that the exposed and unprotected tip of the dilator often becomes frayed as it passes through the tissue track. Such fraying will be cause for additional resistance to entry of the dilator tip into the arteriotomy, as the frayed portion catches on the edge of the arteriotomy impeding passage of the dilator, and creating a larger tear.

Yet another problem encountered is the trauma and tearing of the arterial wall as the blunt dilator tip passes through it. This results in more lengthy and difficult hemostasis at the conclusion of the interventional procedure when all devices are removed from the patient. The size of the post-procedural puncture hole in the blood vessel wall correlates to post-procedural bleeding, time to hemostasis, hematoma formation, and other complications.

Thus, there is a need for a medical filament that eliminates or substantially reduces the abrupt transition or step-up between the filament and a dilator's tip when the dilator is introduced together with and over the filament into a patient, thereby providing smooth dilation of the target orifice. It would be desirable to provide a medical filament that reduces the damage to tissue or blood vessel wall when the dilator is introduced. It would be particularly useful to introduce such a filament and a filament-and-dilator combination adapted for use in the SDH technique.

Objects of the Invention

Accordingly, it is an object of the invention to provide an improved introducing filament to facilitate insertion of a dilator by percutaneous techniques for vascular access, and thereby remedy the deficiencies of the prior art.

It is also an object of the invention to provide apparatus and methods to facilitate insertion of a dilator by percutaneous techniques for vascular access and for accessing other anatomic structures.

It is another object of the invention to reduce or eliminate the step-up in diameter from the introducing guidewire to the distal tip of the dilator.

It is yet another and related object of the invention to reduce or eliminate resistance to advancement of the tip of the dilator through tissues, the tissue track, and into the wall of a blood vessel or into other anatomic structures.

It is yet another object of the invention to reduce or eliminate the uncontrolled entry and its associated trauma, accompanied by the palpable "pop" sensation, as the tip of the dilator overcomes the resistance of the target orifice to insertion.

It is still another object of the invention to reduce or eliminate the fraying and deformation suffered by the tip of the dilator as it is passed through a tissue track to the target orifice, and to reduce or eliminate the additional resistance caused by a frayed or deformed tip as it enters into the target orifice.

It is yet another object of the invention to provide a dilator having a distal tip whose outer diameter is smaller than the outer diameters of the distal tips of known dilators used for comparably-sized guidewires, without sacrificing the structural integrity of the tip, in order to permit the size of initial puncture holes to be reduced.

It is another object of the invention to provide a dilator having a distal tip whose outer diameter is both smaller than the outer diameter of the needle used and smaller than the target orifice created by the puncturing needle.

It is still another and related object of the invention to reduce or eliminate blood backflow through the needle bore resulting from the puncture of the blood vessel by the needle.

It is yet another object of the invention to reduce or eliminate blood backflow from the puncture site around the guidewire, while at the same time reducing or eliminating the step-up in diameter from the introducing guidewire to the tip of the dilator.

It is yet another object of the invention to reduce the force that a practitioner must exert to insert the tip of the dilator during passage of the dilator along a tissue track, and to reduce the force exerted by the tip of the dilator on the tissue track and the wall of the blood vessel.

It is a further object of the invention to reduce or eliminate trauma, or tearing of a blood vessel wall or other anatomic structure when the tip of a dilator is introduced through the puncture.

It is yet another object of the invention to provide a kit of components including a needle, guide element and dilator where the shielding of the dilator tip allows it to be fabricated in the smallest of sizes to access blood vessels and target orifices, as is needed in pediatric and neonatal procedures.

BRIEF DESCRIPTION OF THE DRAWINGS

Several exemplary embodiments of the invention are described below. However, it is to be understood that the invention is not limited to the details of construction or processes set forth in the following description and drawings. The invention is capable of other embodiments and of being practiced or executed in various ways. The drawings are not necessarily drawn to scale, and certain features have been enlarged to depict geometric aspects and relations between features of the various embodiments of the invention. As such, the relative size of various features of embodiments of the invention may be enlarged with respect to other features of the device or parts of the body shown in the drawings.

FIG. 4A shows a longitudinal-sectional view of a filament according to a first embodiment of the invention.

FIG. 4B shows a longitudinal cross-sectional view of a filament in the form of a guidewire according to an embodiment of the invention.

FIG. 6C shows the filament of FIGS. 6A-6B with the dilator tip abutting the annular step transition of the filament as the dilator's tip engages the puncture hole in the blood vessel wall.

FIGS. 9A-9B illustrate filament-dilator coupling mechanisms according to embodiments of the invention.

SUMMARY OF THE INVENTION

Figure 1A:
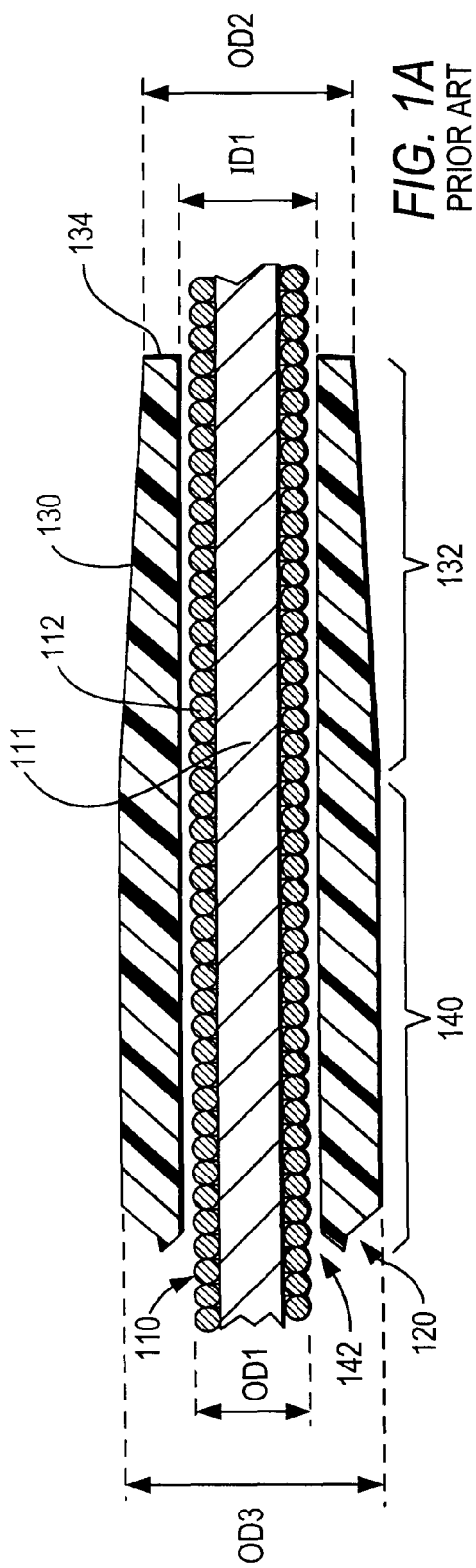
FIGS. 1A and 1B show a partial longitudinal section of a prior-art guidewire and dilator assembly.
Figure 1B:
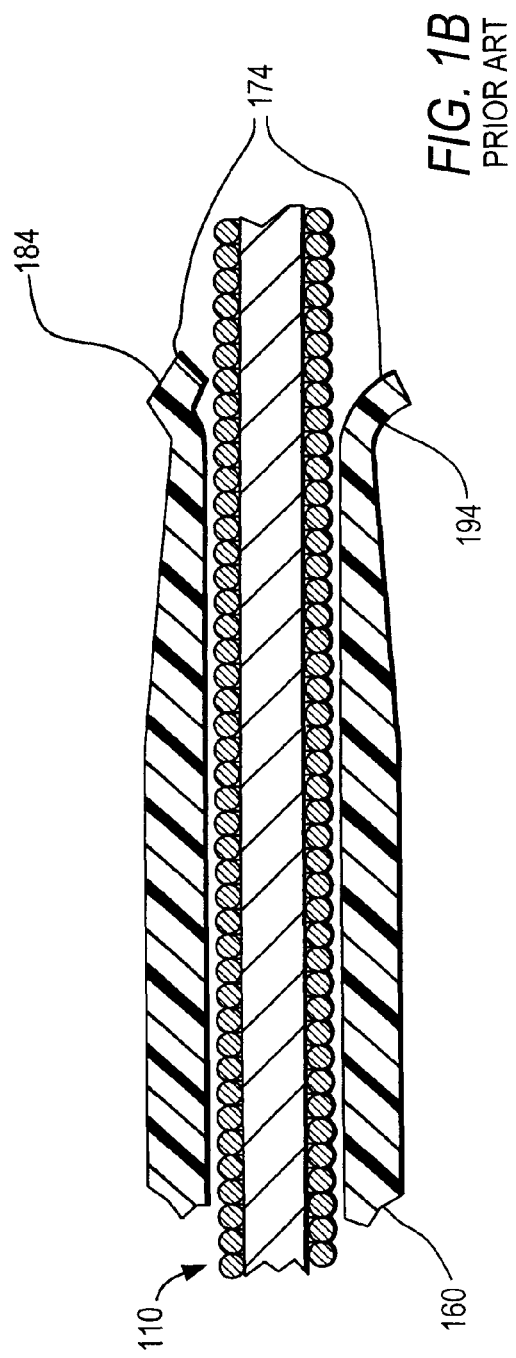
Figure 2A:
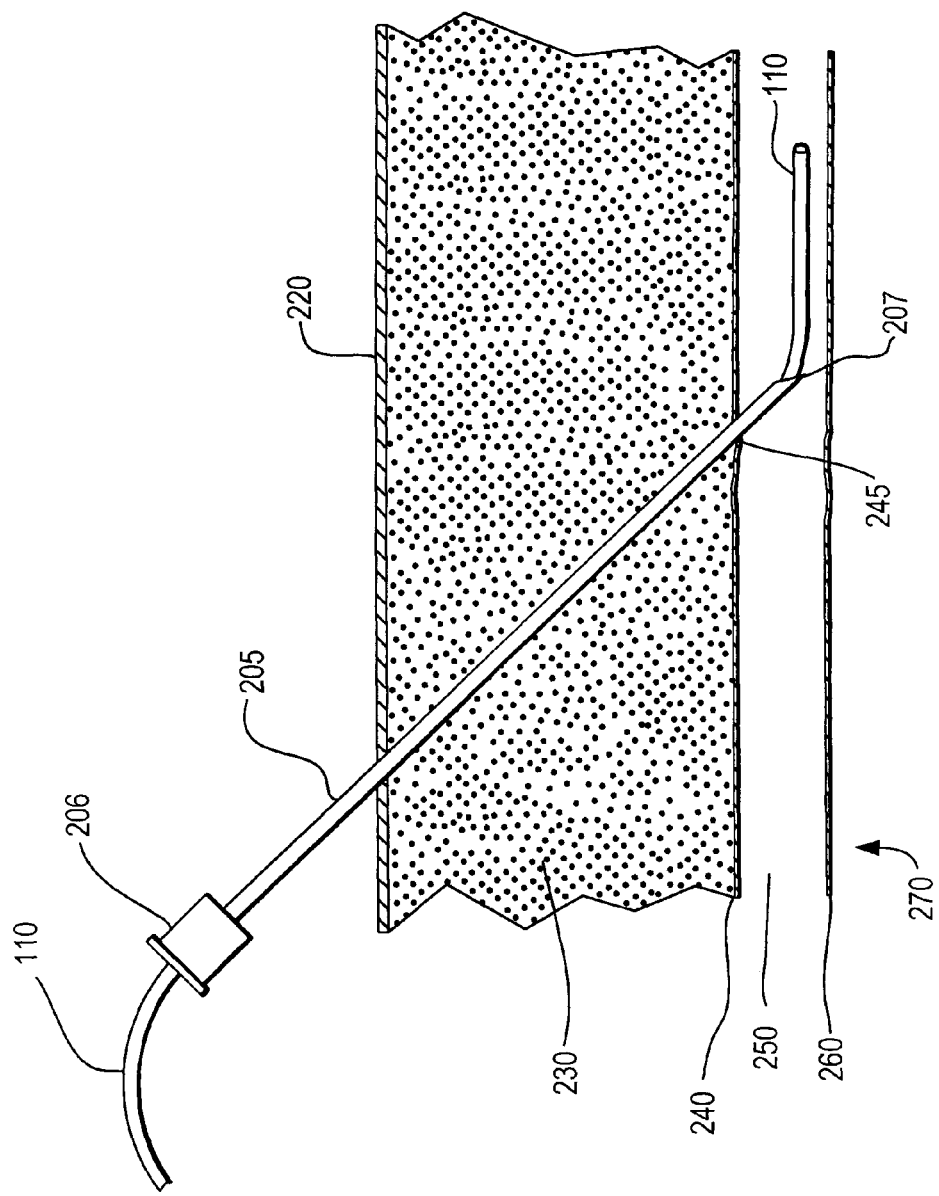
FIG. 2A shows a needle whose tip has been inserted into a patient's blood vessel and a prior-art guidewire residing within the needle according to the SDH technique.
Figure 2B:
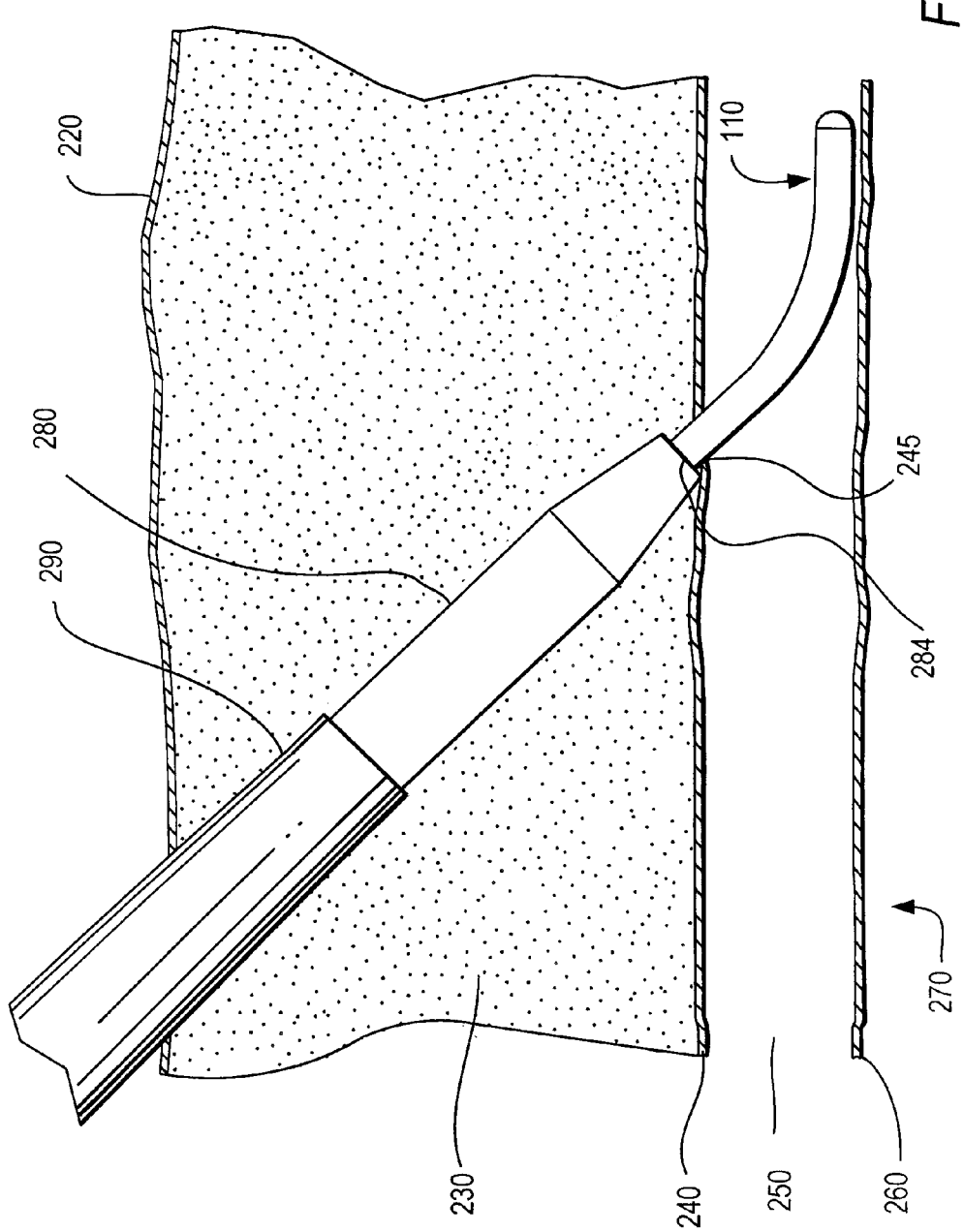
FIG. 2B shows a prior-art guidewire within a patient's blood vessel after the needle has been removed, leaving the guidewire in place with its distal portion residing in the blood vessel, and the dilator with accompanying sheath passing over the proximal end of said guidewire.
Figure 2C:
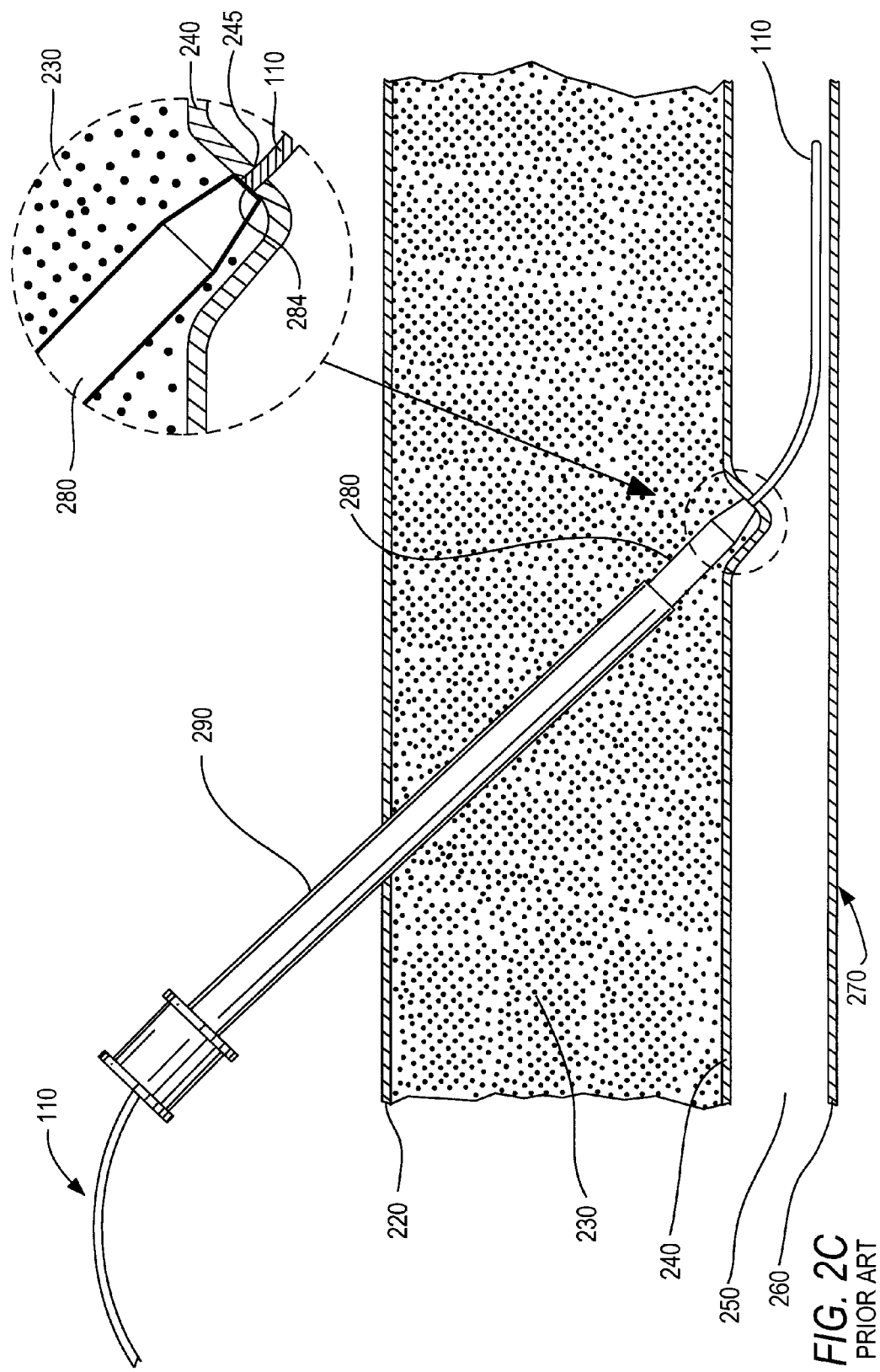
FIG. 2C shows a prior-art guidewire and dilator combination with the distal tip of the dilator engaging the puncture hole in the blood vessel wall created by the needle.

The applicants have developed novel apparatus and methods that are significant improvements over the instruments and procedures previously utilized to implement the SDH technique. They may be advantageously used to access other anatomic structures having passages or hollow cavities such as a kidney, lung, esophagus, pleural cavity, rib cage, cyst or abscess that contains liquid or gas.

Embodiments of the present invention pertain to eliminating, or at least reducing, the step-up or discrete transition from the outer diameter of the prior-art introducing guidewire to the outer diameter of the dilator tip. The inventive filament reduces or prevents trauma to the blood vessel as the combination of these two devices is inserted longitudinally through the tissue track of a patient and into an arteriotomy in a blood vessel. In prior art devices, the discrete step-like increase in diameter from the filament or guidewire to the dilator tip is the principal factor which creates the resistance to entry of the dilator tip into the tissue, and the major cause of trauma and tearing of the arterial wall during procedures involving access to arteries, and as such also results in more lengthy and difficult hemostasis at the conclusion of the procedure when all implements are removed from the patient.

Embodiments of the present invention also create a better match between the diameter of the leading tip of the dilator engaging the vessel wall as the tip more closely approximates the outer diameter of the existing puncture hole, or opening, as created by the puncturing needle, and ideally fits within the perimeter of the existing puncture hole. In a preferred embodiment, this is best accomplished via a mating region between the inventive filament and dilator distal tip with little or no diameter difference, and therefore no step-up between the respective outer diameters of filament distal segment and dilator tip.

The invention is an elongate introducing guide element, or filament, having proximal and distal segments which, at their juncture, form an abrupt, annular, circumferential step transition, the outer diameter of the distal segment adjacent said step being greater than the outer diameter of the proximal segment adjacent said step. The abrupt diameter change creates a proximally-facing circumferential surface at the step transition, which is the proximally-facing end of the distal segment. The outer diameter of the distal segment at the step is also greater than the inner diameter of the mating dilator's opening at its distal tip so that the dilator cannot advance beyond the step, and the tip of the dilator is shielded behind the abrupt circumferential step. The distal segment of the guide element is, or has a portion that is, of sufficient diameter and length to block blood flow through the needle when it is situated inside the bore of the needle, and to block blood flow through the puncture hole after the needle has been removed.

As can be appreciated, the increase in diameter from the guide element to the tip of the dilator in prior-art systems is eliminated. As the guide element and dilator of the invention are advanced together, the guide element effectively shields the tip of the dilator from being abraded or impacted by the tissue along the track leading to the target orifice. The circumferential step also shields the distal tip from the edges of the puncture. When the outer diameters of the tip of the dilator and the step match closely there is a smooth transition from the guide element's distal segment to the dilator's distal tip. This permits the tip and conical portion of the dilator to smoothly enter and dilate a puncture site in an elastic vessel without resistance from the target orifice and without abrupt tearing of the vessel wall.

A further advantage of the step transition is that the diameter of the proximal segment of the introducing filament is reduced relative to prior-art filaments, which in turn permits the lumen of the dilator to be reduced since it now passes over a filament with a smaller diameter. The wall thickness at the dilator distal tip can now also be reduced since it will now be shielded by the step and not subject to fraying and deformation as are the exposed dilator tips of the prior-art. The reduced dilator lumen and reduced wall thickness of the dilator tip permits the dilator tip outer diameter to be significantly reduced relative to prior-art dilators. This allows the initial puncture hole to be made smaller, since it now needs to accommodate a smaller dilator tip, yet still be dilated to the desired size by the dilator. The diameter of the puncturing needle can now also be reduced. The foregoing shows that dilator tips, as well as the entire associated system of components, can now be fabricated in miniaturized sizes not presently available. This is of particular value in pediatric and neonatal procedures where smaller sizes of tools are of paramount importance given the small sizes of the blood vessels being accessed.

Using the apparatus of the preferred embodiment of the invention, a smooth transition between the guide element distal segment and the tip of the dilator is achieved. By utilizing a mating dilator with an outer diameter at its distal tip that is equal or nearly equal to the outer diameter of the distal segment of the guide element adjacent the step, the matching outer diameters provide "equal-shielding" and ensure a smooth transition from the distal segment of the guide element to the tip of the dilator.

According to a second embodiment, the tip of the mating dilator has a smaller outer diameter than the diameter of the distal segment of the guide element at the step. When the two are advanced together distally, the step in the guide element effectively over-shields the distal tip of the dilator. According to a third embodiment, the tip of the dilator has a slightly larger outer diameter than the outer diameter of guide element distal segment adjacent the step. As the dilator and guide element are advanced distally together along the tissue track to and through the target orifice, at least a portion of the thickness of the wall of the distal tip is shielded by the step. This partial shielding allows for a substantial reduction of the increase in diameter from guide element to the tip of the dilator as compared to prior art systems, while still protecting a significant portion of the dilator tip.

The elimination of resistance encountered by the tip of the dilator, whether equally-shielded or over-shielded, prevents both damage to the tip of the dilator and trauma to the tissue track and target orifice. The reduction of resistance encountered by the tip of the dilator when partially-shielded provides a similar benefit.

Preferably, the shape or contour of the tip of the dilator which abuts the step and the shape of the proximally-facing surface of the step are complementary, so that they abut in a contiguous contoured manner. In an alternate embodiment, the tip of the dilator mates or interdigitates with the proximally-facing surface of the step to enhance the mating contact between the dilator tip and the step transition.

The dimensions of the guide element and the dilator are well known to those skilled in the art. By way of example, the outer diameter of the distal segment of the guide element may be from 0.010 to 0.053 inches to match the respective bores for the range of needles used for percutaneous entry, and be from 0.006 to 0.047 inches larger than the outer diameter of the proximal segment of the guide element adjacent the step. The circumferential step has a proximally facing surface, which is the end surface at the proximal end of the distal segment. The plane of that surface is preferably perpendicular to the longitudinal axis of the proximal segment of the guide element, but may be angled proximally between 60 to 90 degrees to the central and longitudinal axis of the proximal segment of the elongate guide element. The maximum outer diameter of the dilator may typically range up to 9 French for the majority of contemporary procedures.

The inventions also include kits. Such kits typically include a needle or other hollow device having a sharp distal tip; an elongate guide element; and a dilator. The kits may also include sheaths.

The inventions also include methods for creating and dilating an opening in the wall of a blood vessel or other anatomical structure. The method is a modification of the SDH technique that includes serial steps starting with inserting a needle, or other sharp tubular device, into the wall of the blood vessel to create the opening. The next step is inserting an elongate guide element of the present invention into the internal bore of the needle or tubular device. The distal segment of the guide element is of sufficient length and diameter to substantially reduce the flow of blood through the internal bore of the needle. A part of the distal segment extends beyond the distal tip of the needle, and therefore extends through the opening in the wall of the blood vessel and into the lumen of the vessel. Preferably the circumferential step is located proximal to the needle hub so that it can be seen and felt by the operator. However, it may optionally reside within the needle bore at any point outside the blood vessel, preferably at a point above skin level. The needle is then slidably removed from the blood vessel while keeping the distal segment of the elongate guide element in the lumen of the blood vessel and the circumferential step outside the blood vessel.

In the next step, a dilator is slid over the proximal segment of the guide element. The dilator has an interior passage of sufficient size to pass over the maximum outer diameter of the proximal segment of the guide element, but not large enough to pass over and beyond the circumferential step. The dilator has a tapered distal end with a distal tip whose outer diameter preferably is not greater than the outer diameter of the distal segment of the guide element at the step. The main body of the dilator has a maximum outer diameter greater than the outer diameter of the distal segment of the elongate element so that it can perform its function of dilating the target opening. The dilator is then advanced along the proximal segment until its distal tip abuts the guide element's circumferential step. Then the elongate guide element and the dilator are advanced together through the opening while maintaining the dilator tip in firm contact with the circumferential step to shield it from intervening tissue and the edges of the opening. The dilator is then advanced farther into the opening to dilate it.

The opening to be dilated need not be created by a needle to benefit from the smooth transition between guide element and dilator provided by the invention. Naturally-occurring openings or portions of an existing passage may be dilated more smoothly with the apparatus of the invention. Alternatively, openings can be created, for example, by cannulas and other tubular instruments, simple incisions, traumatic injury, and the like. Guide elements of the present inventions may include guidewires and other types of filaments

DETAILED DESCRIPTION OF THE PREFERRED EMBODIMENT

A first embodiment of a filament according to the present invention is shown in FIG. 4A. Filament 400 includes a proximal segment 405 and a distal segment 415 which at their juncture form an abrupt, circumferential step 410. Segments 405 and 415 may have the same or different configurations, but cylindrical configurations are preferred for both segments. Distal segment 415 serves multiple purposes: At its proximal end, it forms the abrupt step 410 which shields the distal tip of a dilator; its one or more regions of maximum diameter also block the backflow of blood through the needle, and also block the backflow of blood through the vessel puncture.

Proximal segment 405 has a maximum outer diameter 425 that is preferably substantially constant along the length of proximal segment 405. Distal segment 415 includes tip 420 and a cylindrical elongate portion 440 having a maximum outer diameter 430 that is preferably substantially constant along the length of cylindrical elongate portion 440. At step 410 the distal outer diameter 430, typically in the range of 0.010 to 0.053 inches, is larger than proximal outer diameter 425, typically in the range of 0.006 to 0.047 inches, creating the annular circumferential step. Outer diameter 430 is closely matched to the diameter of the bore of the needle with which filament 400 will be used, and when the respective diameters are properly matched, cylindrical elongate portion 440 will substantially block the backflow of blood from the vessel through the needle bore. Those skilled in the art are familiar with hollow bore needles and matching filaments. Needles for percutaneous entry are typically in the range of 17 g-21 g for adults and 21 g-25 g for pediatrics, and have a corresponding bore of a diameter in the range of 0.012 to 0.057 inches. In the future, the lower end of the range may decrease further as devices are made smaller.

The length of cylindrical elongate portion 440 is broadly from 30 mm, for pediatric uses, to 300 mm. In preferred embodiments, portion 440 is from 70 mm to 150 mm long. Cylindrical elongate portion 440 should be sufficiently long so that at least a significant length, e.g. 20 mm for adult use, can extend from the puncture site into the blood vessel, thereby reducing the backflow of blood from the puncture into the tissue track, and a second length, e.g. 70 mm in adult use, can extend through the bore of the needle. A further additional length, e.g. 30 mm, may extend proximally from the proximal hub of the needle. Cylindrical elongate portion 440 thus serves a shielding-and-blocking function. First, it blocks the backflow of blood through the needle. Second, it subsequently blocks the backflow of blood through the puncture site. Third, it shields the tip of the dilator. Outer diameter 430 preferably remains constant along the length of portion 440 but may vary provided that portion 440 has an appropriate diameter or diameters along its length to perform its blood-blocking functions. Tip 420 is the leading part of distal segment 415. It may have a curved distal end portion resembling the letter "J," commonly referred to as a "J-tip," whose length may generally range from 2 cm to 5 cm.

The total length of filament 400 is preferably 600 mm or less. The total length of the filament of the invention is determined by the combined lengths of the portions of the filament residing in the lumen of the blood vessel, within the needle for its entire length, and outside the needle hub. In an obese patient with a large skin-to-artery distance, the filament would need to be longer. For pediatrics it would be made in a shorter length.

The change in diameter at the juncture of proximal segment 405 and distal segment 415 forms circumferential annular step 410. Preferably, circumferential step 410 is a substantially discrete, abrupt, annular step-down from the larger diameter of distal segment 415 to the smaller diameter of proximal segment 405. Step 410 creates the annular, proximally-facing end-surface 435 which shields the tip of a dilator. The term "proximally-facing" means that the end surface is oriented toward or substantially toward the proximal end of the guide element. The end-surface of step 410 may be perpendicular to the longitudinal axis of the guide element or may be angled to that axis, and may have portions that are not strictly perpendicular to that axis. The end-surface, or portions thereof, may be angled between 60-90 degrees from the longitudinal axis and still be considered proximally-facing.

Surface 435 of step 410 may be angled proximally or distally at 60 to 90 degrees to the longitudinal axis of the guide element. The angle described is that subtended from the longitudinal axis of the proximal segment to surface 435. At angles of less than 90 degrees, proximally-facing surface 435 may have a region with an inwardly conical shape (i.e., a concavity), which captures the tip of a dilator. Alternatively, surface 435 may have an outwardly conical surface which mates with the distal-tip opening of the dilator. Surface 435 may have various planes and shapes provided that it effectively stops the distal movement of an advancing dilator when the dilator abuts the former.

In a preferred embodiment, proximally-facing surface 435 is an annular, ring-shaped, substantially flat surface. Most preferably, proximally-facing surface 435 is geometrically complementary or substantially complementary to the distal surface of the tip of a dilator.

Proximal segment 405 and distal segment 415 may each be made of metal, thermoplastic, composite material or other relatively strong but flexible material, chosen to confer mechanical properties on distal segment 415 which permit it to pass through a hollow-bore needle into a vessel, and to flex to follow the path of the vessel. Manufacturing methods and materials to achieve this purpose are well known in the art. Distal segment 415 may advantageously include a lubricious coating to facilitate its navigation through the bore of a needle and through a vessel.

FIG. 4B illustrates a preferred embodiment of filament 400 in the form of a stepped introducing guidewire 450. Stepped guidewire 450 includes a proximal segment 455 and a distal segment 465 which at their juncture form circumferential step 460. The total length of guidewire 450 is preferably 600 mm or less. Proximal segment 455 has an outer diameter 475 which preferably is substantially constant along its length. The proximal end of distal segment 465 creates step 460 to shield the tip of a dilator. Distal segment 465 also serves to block the backflow of blood through a needle from a vessel puncture.

The term guidewire suggests that it is made from metal (based on the word "wire"), as guidewires currently are. However, with manufacturing advances a guidewire may take on different forms in the future. For example, it may be made entirely from thermoplastic or another type of material that may not normally be considered materials from which to make a wire. Or it may be made from a combination of materials, such as metal and a material such as a thermoplastic material. Structurally, it may be made from a unitary piece of material. Similarly, "core wire", as known in present day guidewire construction, or "core section", may be made from thermoplastic or another material. Thus, it will be understood that alternate embodiments of the filament or guide element can be achieved through the use of various materials other than metal. The term guidewire is used herein to denote any guiding element with the physical properties detailed in this application regardless of the material of which it is made.

As shown in FIG. 4B, proximal segment 455 is advantageously formed from core wire 458, which is a solid wire that extends the length of guidewire 450. Core wire 458 is preferably made of metal, plastic, composite material, or other relatively strong but flexible material so that distal segment 465 can be passed through a hollow needle into a vessel and can flex to follow the path of the vessel. Core wire 458 may comprise a tapered distal end portion 472.

Distal segment 465 has tip 470 and a cylindrical portion 490 with dimensions as described above for distal segment 415 of FIG. 4A. Its functions and characteristics are as described in connection with distal segment 415. Distal segment 465 may include regions of varying flexibility.

As shown in FIG. 4B, distal portion 490 is advantageously formed from coil wire 464 spirally wrapped around core wire 458. Coil wire 464 is preferably made of a flexible material comprised of metal, thermoplastic or composite. Coil wire 464 is most preferably made of a flexible metal having some shape retention qualities and may possess a lubricious surface to facilitate passage through a needle bore and navigation through a blood vessel. Tip 470 may be formed by a hemispherical cap 494. Coil wire 464 may be replaced with a sleeve of suitable material, which may incorporate tip 470. The change in diameter at the junction of proximal segment 455 and distal segment 465 is as described in connection with FIG. 4A, and creates proximally-facing annular end-surface 485, whose functions and characteristics are as described above in connection with proximally-facing surface 435.

In a preferred embodiment, proximally-facing surface 485 of distal segment 465 is a circumferential, ring-like, annulus, with at least a portion of its proximally-facing surface that is substantially flat. The flat surface may be created by various means, for example, by machining a flat surface into the last helical loop 462 of coil wire 464. If a discontinuity in the ring shape naturally results it may be welded or otherwise filled with a suitable material. Alternatively, surface 485 may comprise a single helical loop of coil wire 464. As further alternatives, surface 485 may be provided with an additional structural element to create the proximally-facing surface, such as a circular disc, similar to a washer, to provide a flat surface, or an externally cylindrical section with an inwardly conical-shaped interior, or a cup-shaped piece, a radiographic marker band, radio-opaque element, or the like. FIG. 4B shows surface 485 drawn with a half-coil of last helical loop 462 on the upper side.

Figure 5A:
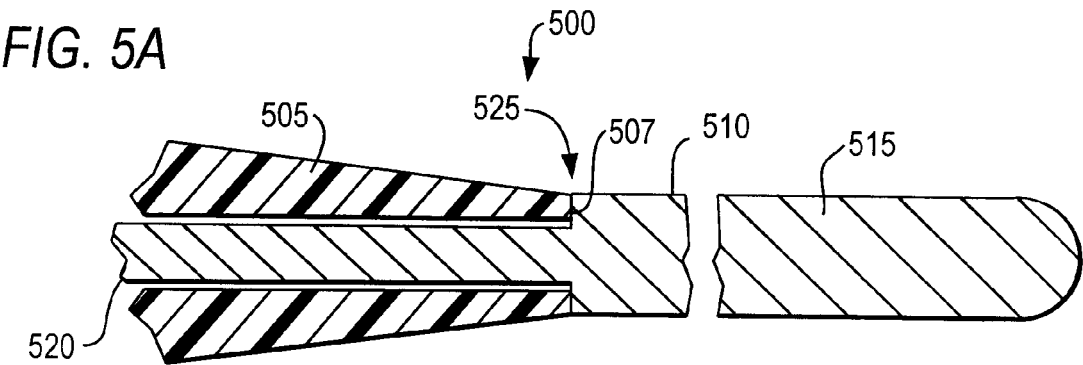
FIG. 5A shows a close-up longitudinal-sectional view of the preferred embodiment of a filament and dilator combination of the invention depicting the exact-shielding of the dilator tip.
Figure 5B:
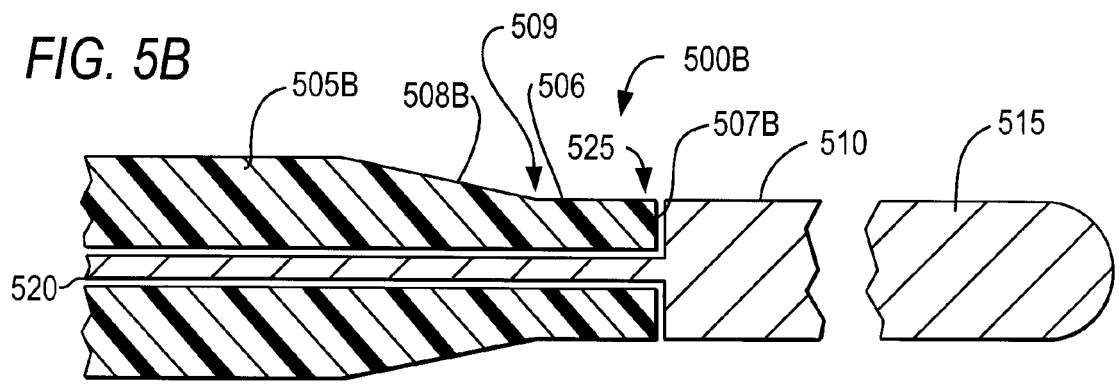
FIG. 5B shows a close-up longitudinal-sectional view of an alternate embodiment of a filament and dilator combination of the invention depicting the exact-shielding of the dilator tip.
Figure 5C:
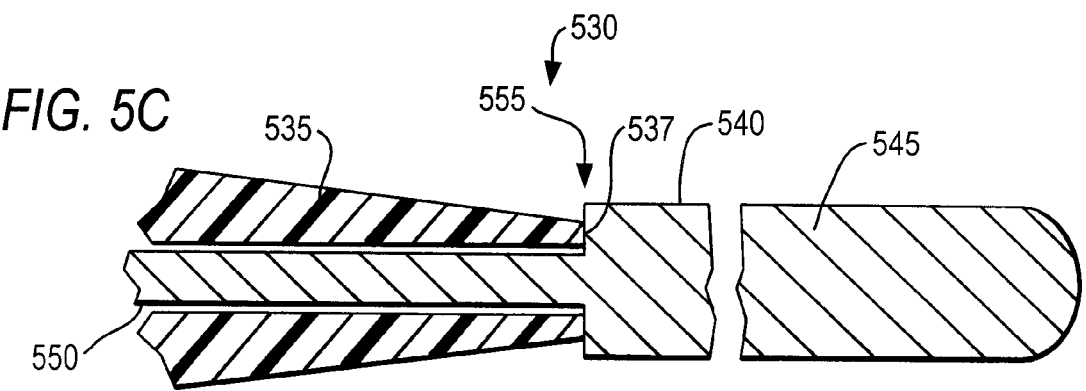
FIG. 5C shows a longitudinal-sectional view of a second embodiment of a filament and dilator combination of the invention depicting the over-shielding of the dilator tip.

FIGS. 5A-5C depicts longitudinal sectional views of assemblies of a filament of the invention and a mating dilator in cooperating relationship. FIG. 5A is a longitudinal cross-sectional view of the combination 500 of a dilator 505 and filament 510 in cooperating relationship. FIG. 5A shows the preferred embodiment which provides equal shielding of the dilator tip 507. The proximal segment 520 of filament 510 is shown fully inserted into dilator 505 so that the distal tip 507 of dilator 505 in an abutting relationship with circumferential step 525. The outer diameter of the tip of dilator 505 matches the outer diameter of distal segment 515 of filament 510 at step 525. When advanced together distally into the patient, distal segment 515 shields the tip 507 of dilator 505, eliminating any discontinuity between filament 510 and the tip 507 of dilator 505, and thereby facilitating a smooth insertion and passage of the dilator and filament combination 500 into a pre-existing puncture hole or orifice.

In this preferred embodiment, the lack of a diameter transition from the outer diameter of the distal segment of the filament to the distal tip of the dilator allows the filament distal segment to fully shield the dilator's distal tip surface. This reduces trauma when inserting the dilator in combination with the filament into a target orifice. The shielded tip of the dilator traverses the tissue track and the target orifice without the resistance experienced with the apparatus of the prior art.

In the preferred embodiment the dilator's increasing taper begins at the distal tip. In alternate embodiments the dilator has an intermediate cylindrical segment between the distal tip and the beginning of the tapered segment. As shown in FIG. 5B, dilator 505B includes cylindrical segment 506 between distal tip 507B and tapered segment 508B.

FIG. 5C is a longitudinal sectional view of the combination 530 of a dilator 535 and filament 540 in cooperating relationship to provide over-shielding of the tip 537 of dilator 535. At the circumferential step 555, the outer diameter of the tip 537 of dilator 535 is smaller than the outer diameter of the distal segment 545 at step 555. Moving in the proximal direction along distal segment 545 to dilator 535, there is a circumferential step down from the outer diameter of distal segment 545 to the outer diameter of the tip 537 of dilator 535. Advanced together distally, the filament's distal segment 545 over-shields the tip 537 of dilator 535. In this embodiment the outer diameter of the distal segment of the filament provides an excessive shield or over-shield for the distal tip. As compared to the guidewire and dilator of the prior art, this embodiment eliminates trauma when inserting a dilator tip in combination with the filament into a target orifice.

Figure 5D:
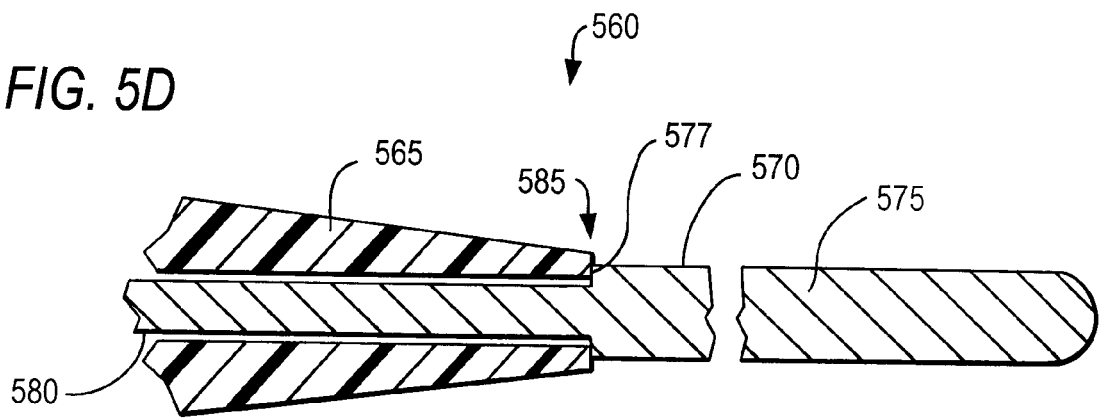
FIG. 5D shows a longitudinal-sectional view of a third embodiment of a filament and dilator combination of the invention depicting the partial-shielding of the dilator tip.

FIG. 5D is a longitudinal sectional view of the combination 560 of a dilator 565 with filament 570 in cooperating relationship to provide partial shielding of the distal tip of dilator 565. The outer diameter of the tip of dilator 565 is larger than the outer diameter of the distal segment 575 of filament 570 at the circumferential step 585, but the inner diameter of the tip of dilator 565 is less than the diameter of distal segment 575 at the step. Therefore the distal tip 577 of dilator 565 is partially shielded by distal segment 575. As compared to the prior-art, this partial-shielding also reduces trauma as the dilator and filament of combination 560 passes through tissue and enters into a target orifice.

As a non-limiting example, a filament with a distal segment of 0.038-inch diameter is compared to a prior-art guidewire with a 0.038-inch diameter. The dilator tip outer diameter is 0.044-inch, which is less than the diameter of a prior art dilator used with a 0.038-inch guidewire, and the tip inner diameter is 0.024-inch. The wall thickness is thus 0.010-inch at the tip. The filament proximal segment has an outer diameter of 0.022-inch to match the dilator's distal tip opening of 0.024-inch. The distal segment outer diameter is 0.038-inch, a common size in the SDH technique. Thus, the annular step on the proximally-facing surface of the distal segment of the filament is 0.008-inch in width, which is half of the difference between 0.022-inch and 0.038-inch. As compared to the prior art, in which the dilator's leading tip is 100% exposed (i.e. 0% shielded), the 0.038-inch diameter annular step of the filament shields 86% of the 0.044-inch diameter dilator tip. Although dilator tip 577 is not completely shielded, this is still a significant improvement over prior-art devices. As can be seen from this example, the dilator leading tip is 86% shielded, as compared to 0% shielding for the prior-art device, and, the outside diameter of the dilator's distal tip is reduced to 0.44-inch as compared to 0.060-inch as described above in paragraph 19 for a comparably sized guidewire 0.038-inch in diameter. This demonstrates that the invention achieves the very important objective of reducing the size of initial puncture holes.

Figure 5E:
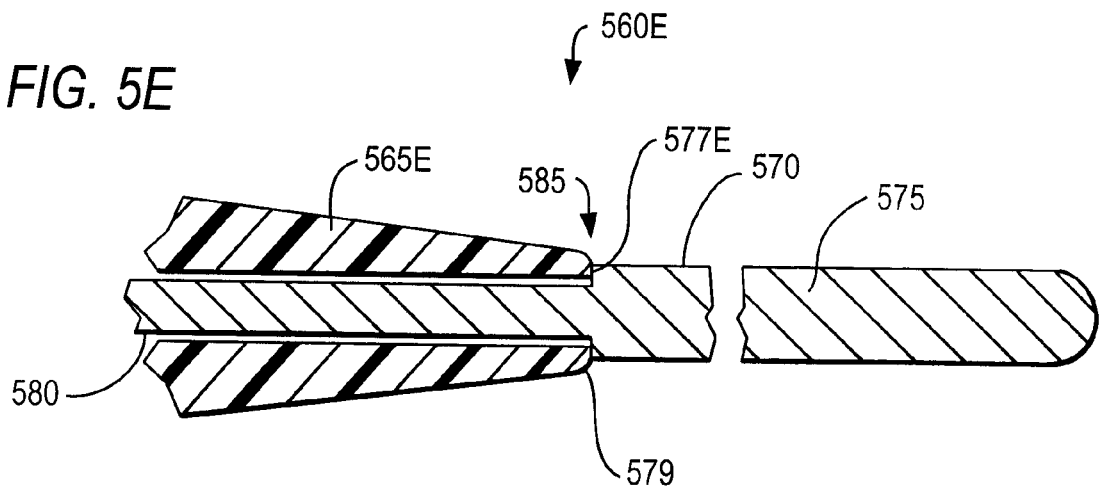
FIG. 5E shows a longitudinal-sectional view of an alternate embodiment of a filament and dilator combination of the invention depicting the partial-shielding of the dilator tip.

In certain embodiments, the tip of the dilator may have a chamfered or rounded outer annular edge. In FIG. 5E, dilator tip 577E of dilator 565E has a chamfered outer annular edge 579, providing a smoother transition from filament to dilator tip.

Figure 6A:
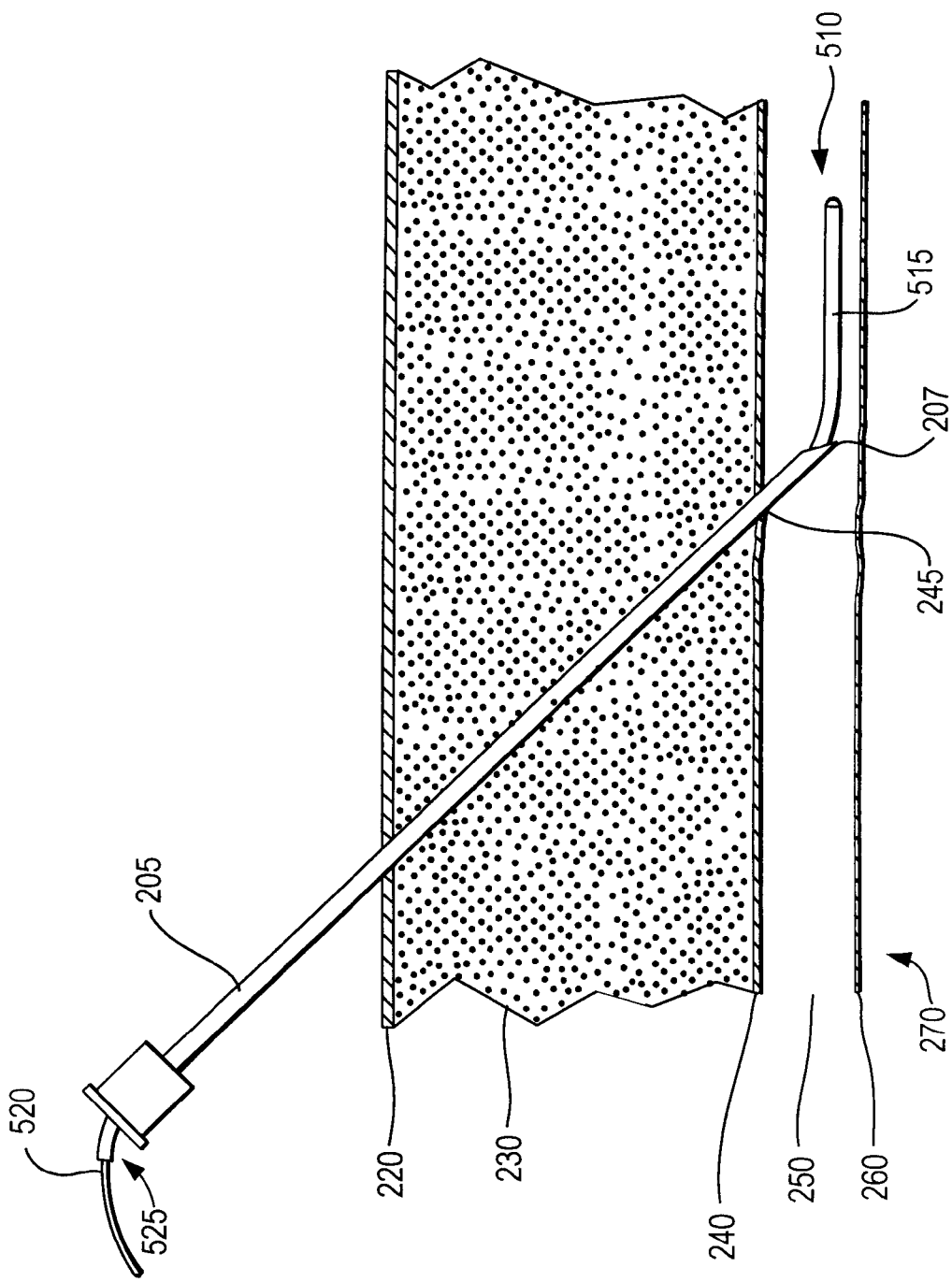
FIG. 6A shows an embodiment of the filament of the invention in use during the percutaneous technique with the filament residing in the hollow bore needle that has been inserted into a blood vessel.
Figure 6B:
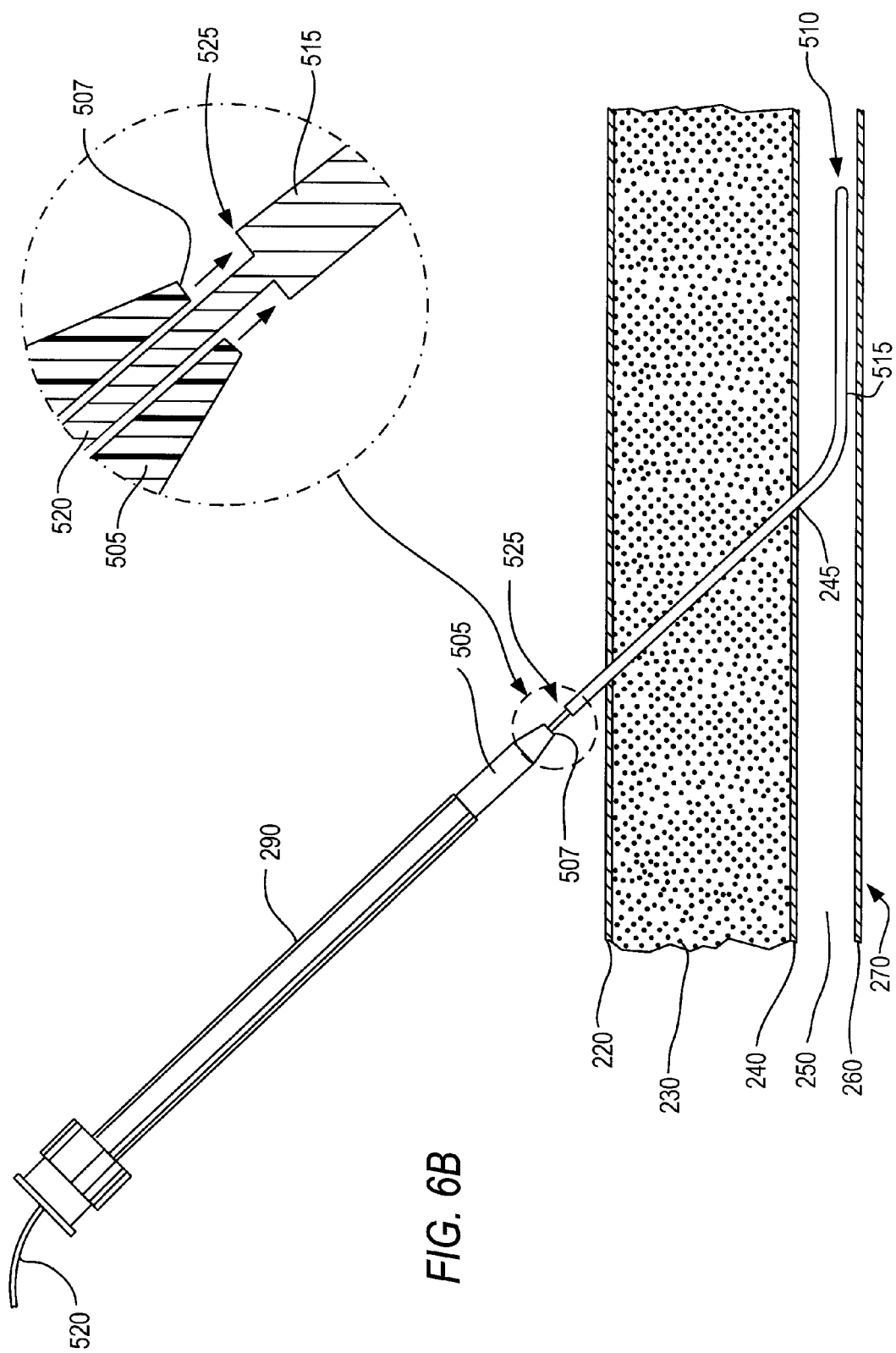
FIG. 6B shows the use of the filament of FIG. 6A in place with a distal portion residing within a blood vessel, and the dilator, with accompanying sheath, being slidably advanced over the proximal end of the filament. The dilator tip is shown approaching the filament's annular step transition.

FIGS. 6A-6C illustrates the use of an embodiment of the invention. The improved SDH technique of the invention includes the steps of penetrating skin 220 with a needle 205, traversing subcutaneous tissue 230 and puncturing wall 240 of blood vessel 270 such that the needle tip 207 lies within the lumen 250 of the blood vessel to provide access to the lumen. Backflow of blood from the vessel through the bore of the needle verifies placement of the needle. Filament 510 is then inserted into the needle hub and advanced through the needle and into lumen 250.

In FIG. 6A filament 510 is positioned such that at least a part of distal segment 515 of filament 510 is positioned in lumen 250 and at least a part is positioned in the bore of the needle 205; at least a part of the proximal segment of filament 510 extends out of the hub of the needle. The circumferential step 525 of filament 510 is preferably positioned proximal to the needle hub so that it can be seen and felt by the operator. However, it may also reside in the needle bore at any point outside the blood vessel, preferably at a point above skin level. In all cases, distal segment 515 substantially fills the inner bore of the needle to prevent the backflow of blood through the bore of the needle. Once filament 510 is in place, the needle is slidably removed over filament 510 without substantially changing the position of the filament.

FIG. 6B depicts the filament positioned in the blood vessel and extending above the skin. In the preferred embodiment, circumferential step 525 is above the skin. The proximal end of filament 510 is then inserted into the longitudinal inner bore of dilator 505. Dilator 505 preferably carries a sheath 290 on the exterior of its main body. Dilator 505 is advanced over the proximal segment of filament 510 until the distal tip 507 abuts the proximally-facing surface of circumferential step 525. The enlarged view within FIG. 6B depicts distal tip 507 approaching step 525. It shows the preferred embodiment in which the two components have matching diameters and therefore provide equal shielding of tip 507. When tip 507 abuts step 525, dilator 505 and filament 510 are advanced together in abutting relationship through skin 220 and subcutaneous tissue 230 to wall 240 of blood vessel 270.

If circumferential step 525 is positioned at or below skin 220, dilator 505 is advanced over the proximal segment of filament 510 until it firmly abuts the proximally-facing surface of step 525. Filament 510 and dilator 505 are then advanced distally together in an abutting relationship to vessel wall 240.

FIG. 6C illustrates the preferred embodiment where the outer diameter of the filament's distal segment 515 at step 525 and the outer diameter of the tip 507 of dilator 505 are substantially equal, providing a smooth transition from filament to dilator while filament and dilator are in abutting relationship. It can be appreciated that this smooth transition eliminates trauma to the tip of the dilator and to the walls of the tissue track. Due to the equal shielding of the tip 507 by circumferential step 525 of filament 510, the tip 507 of dilator 505 penetrates the vessel wall 240 through the puncture previously created by the needle without localized trauma or distension of the vessel wall at the moment of initial entry of the dilator tip into and through the puncture 245. Desirably, the transition between filament and dilator is smooth such that no palpable "pop" sensation is felt by the operator as the dilator first enters the puncture.

As dilator 505 is advanced farther, the conical taper of the dilator's distal portion smoothly dilates puncture 245 to accommodate the larger outer diameter of the main body of dilator 505. Sheath 290 is then advanced in tandem with dilator 505 through skin 220, tissue 230 and vascular wall 240 until a distal portion of sheath 290 is located well within vessel lumen 250. The filament 510 and dilator 505 are then removed, leaving sheath 290 in place to provide an open channel to lumen 250. A practitioner may then insert a diagnostic or therapeutic catheter or other devices into vessel lumen 250 via sheath 290.

Figure 3A:
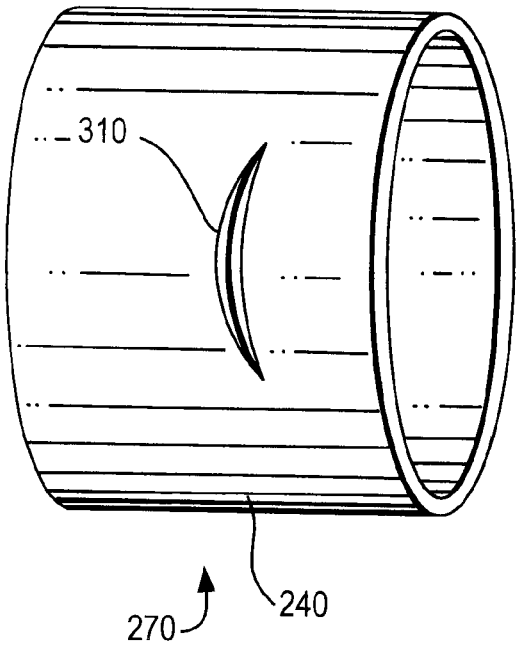
FIG. 3A illustrates a puncture in a vessel caused by insertion of a beveled needle according to the prior-art SDH technique.
Figure 3B:
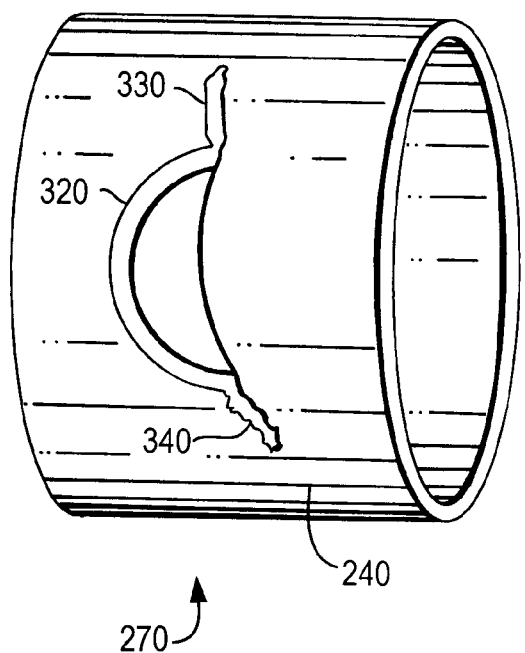
FIGS. 3B and 3C illustrate a torn, traumatized puncture in a vessel caused by insertion of a dilator over a guidewire according to the prior-art SDH technique.
Figure 3C:
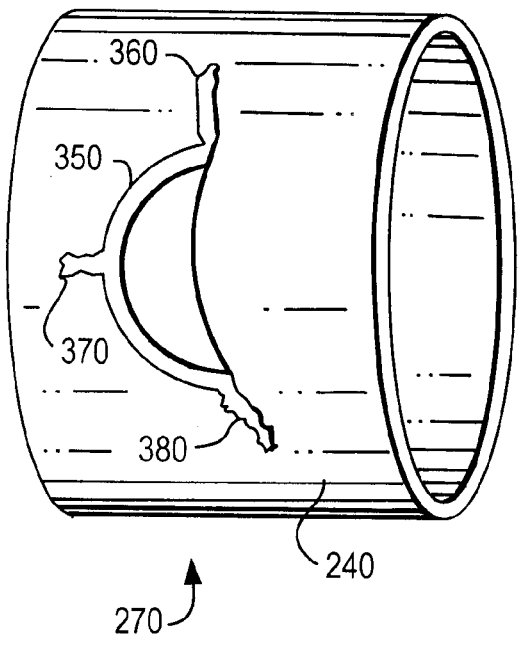
Figure 3D:
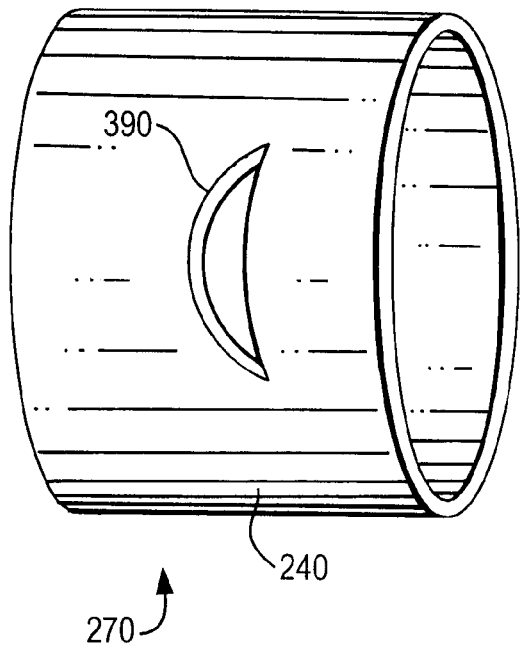
FIG. 3D illustrates a puncture caused by insertion of a dilator and guidewire according to an embodiment of the invention.

FIG. 3D is a top view of the resulting opening 390 in blood vessel 270 after it is punctured by a beveled needle and dilated by dilator 505 which has been fully shielded by step 525. As can be appreciated in FIG. 6C, as the tapered portion of dilator 505 is advanced into and through the puncture 245, the puncture dilates smoothly, and tearing of vessel wall 240 is reduced or eliminated. The resultant opening 390 in vessel wall 240 is both smaller and smoother than openings 320 or 350 created by the prior art methods and apparatus as depicted in FIGS. 3B and 3C. If tearing of the puncture does occur, presumably due to the elastic limitations of vessel wall 240, such tearing is less severe than that created by a conventional prior-art dilator-filament combination.

Other embodiments of the invention include mating configurations of the circumferential, annular step transition of the filament and the tip of the dilator which improve the connection of the two upon abutment of the dilator tip to the step. FIGS. 7A-7C and 8A-8C show these features.

Figure 7A:
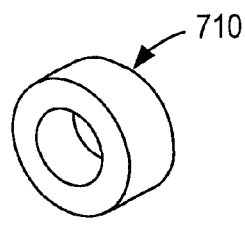
FIGS. 7A-7C show several elements for use at the filament's annular step transition to facilitate shielding of the dilator tip.
Figure 7B:
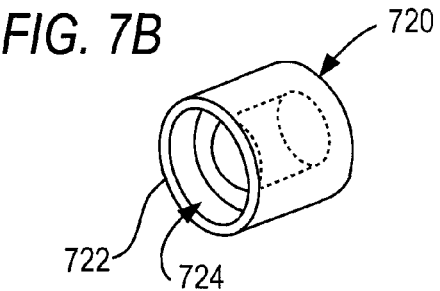
Figure 7C:
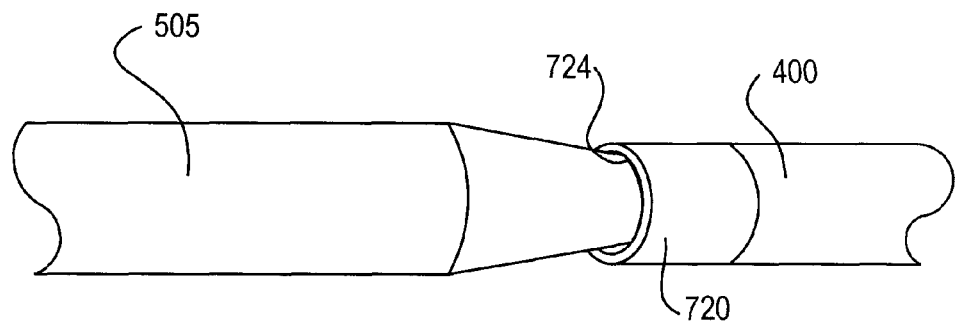

In one embodiment an element is affixed to or is an integral part of the proximally-facing surface of the step which mates with the distal tip of the dilator. The proximally-facing surface of such a transition element then becomes the proximally-facing surface of the step, or a portion thereof. An advantage of a separate transitional element is that its proximally-facing surface can be fabricated to be very precise and smooth so that it will not damage the tip of the dilator. Another advantage is that a specific surface, shape, or contour can be created which, for example, may be complementary to the tip of the dilator. FIGS. 7A-7C show examples of such transitional elements. FIG. 7A illustrates a transition element 710 for use at the proximally facing surface of the step of a filament. Transition element 710 is a cylindrical, annular element similar to a disc or flat washer. It provides a flat, smooth mating surface for the tip of a dilator when the filament and dilator abut one another.

FIG. 7B illustrates a transition element 720 for use at the proximally facing surface of the circumferential step of a filament of the invention when the step over-shields the dilator tip. Transition element 720 is a cylindrical shell with a recessed, proximally-facing annular surface. Transition element 720 includes outer annular rim surface 722 and recessed inner annular surface 724. Transition element 720 thus provides a recessed, cup-shaped, mating surface for abutting and capturing the tip of a dilator, and thereby totally protects the dilator's tip when the filament and dilator are assembled. The recess or "cup" of transition element 720 is sized to capture a leading portion of the tip of the dilator. FIG. 7C illustrates transition element 720 assembled onto filament 400 and capturing the tip of dilator 505. Transition element 710 may be assembled in similar fashion. In all embodiments of the cup-shaped feature, the interior of the recess or cup may be of various shapes that accommodate the dilator tip.

Figure 8A:
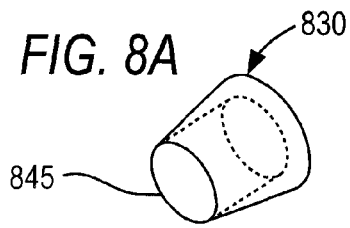
FIGS. 8A-8C show several elements for use at the filament's annular step transition to more precisely center the dilator on the filament.

Embodiments of the invention may further include an element residing in the step transition region for firmly centering the dilator tip relative to the circumferential step. FIG. 8A illustrates a hollow, conical-shaped, transition element 830. The outer diameter at the base of conical transition element 830 is substantially equal to the inner diameter of the distal tip of the dilator so that the conical structure can fit inside the tip and center the dilator on the filament. Positioned with its base abutting the end-surface of the proximally facing step of the filament, transition element 830 serves as a positive centering guide for an abutting dilator tip.

Figure 8B:
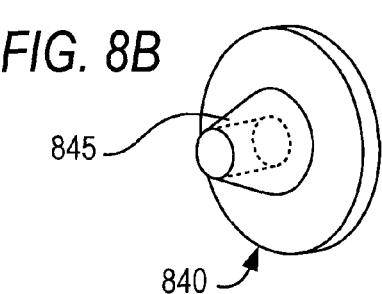

The conical centering portion 835 penetrates inside the tip of the dilator to assure optimum concentricity of dilator tip relative to the distal segment of the filament. A central protrusion on the end-surface may be achieved in other ways by various techniques of manufacture. FIG. 8B depicts a centering element incorporated into a transition element similar to transition element 710. Transition element 840 comprises a conical portion 845 incorporated into a washer. Transition elements 710, 720, 830 and 840 may possess a central bore whose diameter matches or is slightly greater than the outer diameter of the proximal segment of the filament. Transition elements 710, 720, and 840 have an outer diameter that is preferably equal to, but in certain cases is less than, the outer diameter of the distal segment of the filament adjacent to the step. It should be noted that various tapers and rounded contours may also achieve such concentricity of the dilator's tip.

Figure 8C:
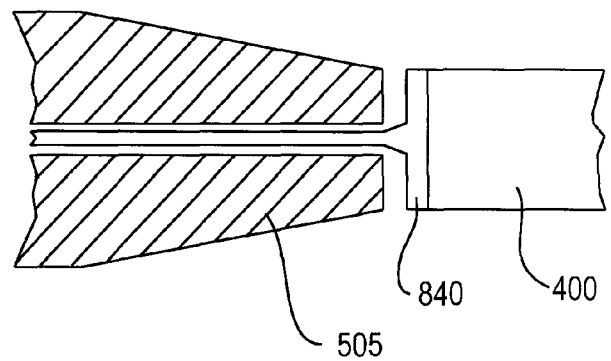

FIG. 8C shows transition element 840 affixed to the proximally-facing surface of the distal segment of the filament 400. Transition elements 710, 720 and 730 are affixed to the proximally-facing surface of the distal segment of the filament in a similar fashion. Transition elements 710, 720, 830 and 840 may be adhered, bonded, welded, soldered, or otherwise affixed to the proximal surface of the distal segment of a filament.

Embodiments of the invention may further include coupling mechanisms to secure the filament to the dilator in an abutting relation to facilitate their joint advancement along the tissue track. The dilator may include an integrated coupling incorporated into its hub or incorporated into a separate structure that is itself coupled to the hub of the dilator. This coupling can be achieved, for example, with an elastomeric compression element that surrounds and engages the filament and compresses against it. This includes a cylindrical gasket having a hollow bore into which the proximal segment of the filament is positioned. Mechanical means are provided to compress the elastomeric element around and against the filament such that the frictional force is sufficient to prevent any relative movement of the filament within the compression element. An example of such a coupling is the well-known Touhy-Borst Adapter.

Alternatively, as shown in FIG. 9A, coupling is accomplished by a knurled screw-down, bolt-like element 910. The threaded bolt 912 is contained within a housing 914 through which filament 510 passes. The housing is positioned in an abutting relationship with the hub of dilator 505. The bolt's tip (not shown) exerts a compressive force against the filament. The bolt can be tightened until the frictional force is great enough to prevent relative movement of the filament and the dilator. A similar compressive force may be attained by a manual or spring-loaded clamp which is released within a housing to exert a compressive force against the filament.

The inventions may include other types of coupling mechanisms to secure the filament to the dilator when they are assembled. Such mechanisms ensure that the dilator and filament are advanced together and do not move relative to one another, so that firm abutment of dilator tip to step is maintained for ideal shielding. These coupling mechanisms may be integrated into one of the components or be a separate element that is attached to the assembly after the dilator tip abuts the filament's step transition. One alternate embodiment, shown in FIG. 9B, is a tight-fitting, frictional, notched fastener 930, which may be similar in design to a clothespin, or may have a triangulated notch 932. This fastener is assembled onto the filament at a position adjacent the dilator's hub and pressed until it reaches a point within the notch that provides a tight grasp onto the filament. The fastener is positioned in an abutting relationship with the hub of dilator 505. Alternatively, the frictional element may be a clip mechanism.

In other exemplary embodiments the proximal segment of the filament or a portion thereof may have its surface abraded, roughened, or otherwise treated to increase the frictional force between the coupling element and filament to prevent slipping. This treatment may be limited to a small area where the guide element exits the back end of the dilator hub, a preferred location for a coupling mechanism to be placed. An apparatus wherein said introducing guide element comprises a distal tip and includes at least one marking to indicate the distance from said distal tip.

An elongate guide element having a proximal segment and a distal segment which at their juncture form an abrupt, circumferential step comprising an annular proximally-facing surface said distal segment having a portion of maximum diameter that is at least 3 millimeters in length to block the flow of fluid through said opening when said guide element resides within said opening.

Each dilator shown and discussed above has a tapered region at its distal end. As will be understood by the skilled artisan, certain other functional catheter types do not taper, but rather have a uniform outer diameter at their distal end. Filaments similar to those described can be used with catheters having a uniform diameter at their distal end and serve to reduce or eliminate the discontinuity between the filament and such catheters.

Each dilator shown and discussed above has been described in its simplest construction with a centric lumen. As will be understood by the skilled artisan, certain other functional catheter types may have a lumen that is eccentric, or may have multiple lumens. Filaments similar to those described can also be constructed to have its proximal segment be eccentric from the central axis of the distal segment in order to mate with an eccentric lumen in a catheter, yet still serve to reduce or eliminate the discontinuity between the filament and such catheters It will be appreciated from the foregoing that the invention eliminates or substantially reduces the step-up in diameter at the advancing tip of a prior-art dilator, hence eliminating the blunt insertion force required by prior-art apparatus and the resulting trauma to and tearing of the arterial wall at the puncture hole. Embodiments of the present invention provide for a smoother and less traumatic passage of the dilator tip through the tissue and vessel puncture hole by providing shielding of the dilator tip.

Although the classical percutaneous SDH technique was originally developed for entry into the femoral artery, more recently this technique has been applied to other peripheral arteries which are accessible beneath the skin. The foremost example of such an alternate arterial site is the radial artery at the wrist. The radial artery has become the second most frequent percutaneous entry site for coronary angiography and intervention. Although not as large in diameter as the femoral artery, the radial artery lies closer to the surface of the skin, is more easily palpated and entered by the puncturing needle. Access via the radial artery has the additional benefit of allowing the patient to ambulate earlier than where access is via the femoral artery in the thigh. Other sites where the percutaneous technique is performed include superficial veins, such as the femoral, brachial, or jugular. The apparatus of the invention are also applicable to accessing these other peripheral blood vessels

What is claimed is:

1. An apparatus for percutaneously dilating an opening in the wall of a blood vessel or other anatomic structure comprising, in combination:
    an elongate introducing guide element having a proximal segment and a distal segment which meet at a juncture, said proximal segment having a first outer diameter at said juncture and said distal segment having a second outer diameter at said juncture greater than said first outer diameter, thereby forming an abrupt circumferential step comprising a proximally-facing surface such that said step creates a discrete transition between said proximal segment and said distal segment,
    said distal segment comprising a distal tip and an elongate portion extending from said step to said distal tip of said distal segment; wherein said guide element comprises an introducing guidewire having a maximum outer diameter of 0.038-inch or less; and a dilator matched to said introducing guide element having an interior bore of sufficient size to permit said dilator to slide over the entire proximal segment of said introducing guide element, said dilator comprising a distal tip having a distally-facing annular surface with an opening into said interior bore, said dilator distal tip having an inner diameter less than said second diameter, such that when assembled together said dilator cannot pass distally beyond said step, said dilator distal tip having an outer diameter substantially equal to said second outer diameter, such that that when assembled together with said dilator distal tip abutting said step their respective outer diameters match one another to provide precise shielding of said dilator distal tip and a smooth transition from said introducing guide element distal segment outer diameter to said dilator distal tip outer diameter, thereby permitting said dilator distal tip to smoothly enter said opening without resistance from said wall of said blood vessel or anatomic structure.

2. An apparatus as recited in claim 1 wherein at least a portion of said proximally-facing surface of said step is substantially perpendicular to a central longitudinal axis of said proximal segment.

3. An apparatus as recited in claim 1 wherein at least a portion of said proximally facing surface of said step is angled proximally or distally at 60 to 90 degrees to the central and longitudinal axis of the introducing guide element.

4. An apparatus as recited in claim 1 wherein said distal segment has a length of 300 millimeters or less and said proximal segment has a length of 300 millimeters or less.

5. An apparatus as recited in claim 1 wherein said distal segment has a portion of maximum diameter that is at least 3 millimeters in length to block the flow of fluid through said opening when said portion of maximum diameter resides within said opening.

6. An apparatus as recited in claim 1 wherein said proximally-facing surface of said step includes a proximally-extending conical portion having a base adjacent said step, said base having a diameter less than the outer diameter of said distal segment adjacent said step.

7. An apparatus as recited in claim 1 wherein said proximally-facing surface of said step comprises a proximally-facing contoured surface, and said distal tip of said dilator comprises a distally-facing surface substantially complementary to said proximally-facing contoured surface.

8. An apparatus as recited in claim 1 wherein said proximally-facing surface of said step comprises means to capture the distal tip of said dilator.

9. An apparatus as recited in claim 1 further including means for coupling said introducing guide element to said dilator.

10. An apparatus as recited in claim 9 wherein said dilator and said introducing guide element are assembled together, with said dilator distal tip abutting said step, and coupled to each other.

11. An apparatus as recited in claim 1 further including a coupling mechanism to couple said introducing guide element to said dilator.

12. An apparatus as recited in claim 11 wherein said dilator includes a hub and said coupling mechanism comprises an element assembled onto said introducing guide element and adapted to engage with the hub of said dilator.

13. An apparatus as recited in claim 11 wherein said dilator comprises a compression mechanism adapted to engage said introducing guide element.

14. An apparatus of claim 11 wherein said proximal segment of said introducing guide element comprises a region with a roughened surface to interface with said coupling mechanism.

15. An apparatus of claim 1 further comprising a separate annular transition element that is adhered to the proximally facing surface of said step.

16. The apparatus of claim 15 wherein said transition element is cylindrical.

17. An apparatus of claim 1 wherein said dilator has a maximum outer diameter of 9 French and said introducing guide element comprises an introducing guidewire with a distal segment having a maximum outer diameter of 0.038-inch.

18. An apparatus of claim 1 wherein said introducing guide element includes at least one marking to indicate the distance from said distal tip of said introducing guide element.

19. An apparatus of claim 1 further including a coupling mechanism to couple said introducing guide element to said dilator when said guide element and said dilator are assembled together in an abutting relationship, said distal segment having a portion of maximum diameter that is at least 3 millimeters in length to block the flow of fluid through said opening when said guide element resides within said opening.

20. An apparatus as recited in claim 1 wherein said proximal segment of said elongate guide element is a core wire, and said distal segment of said elongate guide element comprises said core wire and a second wire coiled around said core wire, the last helical coil at the proximal end of said distal segment being fabricated flat to comprise a portion of said proximally-facing surface.

21. An apparatus as recited in claim 1 further including an introducing sheath, said sheath sized to fit over and around the body of said dilator so as to be carried in tandem with said dilator during insertion into said opening, wherein said dilator may be removed from within said sheath by pulling it proximally from said sheath.

22. An apparatus as recited in claim 1 wherein said blood vessel is the femoral artery.

23. An apparatus for percutaneously dilating an opening in the wall of a blood vessel or other anatomic structure comprising:

an elongate introducing guide element having a proximal segment and a distal segment which meet at a juncture, said proximal segment having a first outer diameter at said juncture and said distal segment having a second outer diameter at said juncture greater than said first outer diameter, thereby forming an abrupt circumferential step comprising an proximally-facing surface such that said step creates a discrete transition between said proximal segment and said distal segment, said distal segment having a portion of maximum outer diameter that is at least 3 millimeters in length to block the flow of fluid through said opening when said portion of maximum outer diameter resides within said opening; and a dilator having an interior bore of sufficient size to permit said dilator to slide over the entire proximal segment of said introducing guide element, said dilator comprising a distal tip having a distally-facing annular surface with an opening into said interior bore, said dilator distal tip having an inner diameter less than said second diameter, such that when assembled together said dilator cannot pass distally beyond said step.

24. An apparatus as recited in claim 23 wherein said introducing guide element includes at least one marking to indicate the distance from the distal tip of said introducing guide element.

25. An apparatus as recited in claim 23 wherein said distal segment comprises a wire coiled around a longitudinal core element and said proximal portion is solely comprised of said core element.

26. An apparatus as recited in claim 23 wherein at least a portion of said proximally-facing surface of said step is substantially perpendicular to a central longitudinal axis of said proximal segment.

27. An apparatus as recited in claim 23 wherein said distal segment has a minimum length of 1.0-inches to assure that said distal segment has sufficient length to extend through said opening in said wall of a blood vessel or other anatomic structure and assure that said step resides outside said opening in said wall of a blood vessel or other anatomic structure.

28. An apparatus as recited in claim 23 wherein said blood vessel is the femoral artery.

29. An apparatus as recited in claim 23 wherein said proximal segment of said elongate guide element is a core wire, and said distal segment of said elongate guide element comprises said core wire and a second wire coiled around said core wire, the last helical coil at the proximal end of said distal segment being fabricated flat to comprise a portion of said proximally-facing surface.

30. An apparatus as recited in claim 23 wherein said portion of maximum diameter is of a diameter greater than the outer diameter at another portion of said distal segment of said introducing guide element.

31. An apparatus as recited in claim 23 wherein said proximally-facing surface of said step comprises a proximally-facing contoured surface, and said distal tip of said dilator comprises a distally-facing surface substantially complementary to said proximally-facing contoured surface.

32. An apparatus as recited in claim 23 further including an introducing sheath, said sheath sized to fit over and around the body of said dilator so as to be carried in tandem with said dilator during insertion into said opening, wherein said dilator may be removed from within said sheath by pulling it proximally from said sheath.

33. An apparatus as recited in claim 23 further including means for coupling said introducing guide element to said dilator.

34. An apparatus as recited in claim 33 wherein said dilator and said introducing guide element are assembled together, with said dilator distal tip abutting said step, and coupled to each other.

35. A kit containing components of an apparatus for percutaneously creating and accessing an opening in the wall of a blood vessel or other anatomical structure comprising, in combination:
a tubular device having a sharp distal tip and a hollow bore for percutaneous puncture of said wall to create said opening; and
an elongate introducing guide element for passage through said tubular device to access said opening, said introducing guide element having a proximal segment and a distal segment which meet at a juncture, said proximal segment having a first outer diameter at said juncture and said distal segment having a second outer diameter at said juncture greater than said first outer diameter, thereby forming an abrupt circumferential step comprising a proximally-facing surface such that said step creates a discrete transition between said proximal segment and said distal segment,
said distal segment having a portion of maximum outer diameter,
said maximum outer diameter matched to the diameter of the hollow bore of said tubular device, thereby blocking the flow of fluid through said hollow bore when said portion of maximum outer diameter resides within said hollow bore,
said portion of maximum outer diameter being at least 3 millimeters in length to block the flow of fluid through said opening when said needle is removed and said portion of maximum outer diameter resides within said opening.

36. A kit of claim 35 wherein said tubular device is a vascular needle.

37. A kit of claim 35 wherein said distal segment has a maximum outer diameter of 0.053-inch or less.

38. An apparatus as recited in claim 35 wherein said portion of maximum diameter is of a diameter greater than the outer diameter at another portion of said distal segment of said introducing guide element.

39. An apparatus as recited in claim 35 wherein said distal segment has a portion of maximum diameter that is at least 3 millimeters in length to block the flow of fluid through said opening when said portion of maximum diameter resides within said opening.

40. A kit containing components of an apparatus for percutaneously creating and dilating an opening in the wall of a blood vessel or other anatomical structure comprising:
a needle having a hollow bore for percutaneous puncture of said wall to create said opening; and
an elongate introducing guide element for passage through said needle to access said opening, said introducing guide element having a proximal segment and a distal segment which meet at a juncture, said proximal segment having a first outer diameter at said juncture and said distal segment having a second outer diameter at said juncture greater than said first outer diameter, thereby forming an abrupt circumferential step comprising a proximally-facing surface such that said step creates a discrete transition between said proximal segment and said distal segment,
said distal segment comprising one or more portions having an outer diameter matched to the diameter of said hollow bore of said needle to permit it to block the flow of fluid through the hollow bore of said needle when said distal segment is positioned therein; and
a dilator having an interior bore of sufficient size to permit said dilator to slide over the entire proximal segment of said introducing guide element,
said dilator comprising a distal tip having a distally-facing annular surface with an opening to said interior bore,
said dilator distal tip having an inner diameter less than said second diameter, such that when assembled together said dilator cannot pass distally beyond said step,
said dilator distal tip having an outer diameter substantially equal to said second outer diameter, such that that when assembled together with said dilator distal tip abutting said step their respective outer diameters match one another to provide precise shielding of said dilator distal tip and a smooth transition from said introducing guide element distal segment outer diameter to said dilator distal tip outer diameter, thereby permitting said dilator distal tip to smoothly enter said opening without resistance from said wall of said blood vessel or anatomic structure.

41. An apparatus as recited in claim 40 wherein said blood vessel is the femoral artery.

42. An apparatus as recited in claim 40 further including an introducing sheath, said sheath sized to fit over and around the body of said dilator so as to be carried in tandem with said dilator during insertion into said opening, wherein said dilator may be removed from within said sheath by pulling it proximally from said sheath.

43. An apparatus as recited in claim 40 wherein at least a portion of said proximally-facing surface of said step is substantially perpendicular to a central longitudinal axis of said proximal segment.

44. An apparatus as recited in claim 40 wherein at least a portion of said proximally facing surface of said step is angled proximally or distally at 60 to 90 degrees to the central and longitudinal axis of the introducing guide element.

45. An apparatus as recited in claim 40 further including a coupling mechanism to couple said introducing guide element to said catheter dilator.

46. An apparatus as recited in claim 40 wherein said proximally-facing surface of said step comprises a proximally-facing contoured surface, and said distal tip of said dilator comprises a distally-facing surface substantially complementary to said proximally-facing contoured surface.

47. A kit containing components of an apparatus for percutaneously creating and dilating an opening in the wall of a blood vessel or other anatomical structure comprising:
   a needle having a hollow bore for percutaneous puncture of said wall to create said opening;
   an elongate introducing guide element for use with said needle having a proximal segment and a distal segment which meet at a juncture, said proximal segment having a first outer diameter at said juncture and said distal segment having a second outer diameter at said juncture greater than said first outer diameter thereby forming an abrupt circumferential step comprising a proximally-facing surface such that said step creates a discrete transition between said proximal segment and said distal segment,
   said distal segment having a portion of maximum outer diameter that is at least 3 millimeters in length and of a diameter to permit it to block the flow of fluid through said hollow bore of said needle when positioned therein and to block the flow of fluid from said opening when said needle is removed and said portion of maximum outer diameter resides within said opening; and
   a dilator having an interior bore of sufficient size to permit dilator to slide over the entire proximal segment of said introducing guide element,
   said dilator having a distal tip having a distally-facing annular surface with an opening to said interior bore,
   said dilator distal tip having an inner diameter smaller than said second diameter,
   such that when assembled together said dilator cannot pass distally beyond said step.

48. A kit as recited in claim 47 further including an introducing sheath, said sheath sized to fit over and around the body of said dilator so as to be carried in tandem with said dilator during insertion into said opening, wherein said dilator may be removed from within said sheath by pulling it proximally from said sheath.

49. A kit of claim 47 wherein said hollow bore has a maximum diameter of 0.020-inch and said proximal segment has a maximum diameter of 0.010-inch.

50. An apparatus of claim 47 wherein said dilating catheter distal tip has an outer diameter substantially equal to the outer diameter of said distal segment adjacent said step.

51. An apparatus of claim 47 wherein said dilating catheter distal tip has an outer diameter smaller than the outer diameter of said distal segment adjacent said step.

52. An apparatus of claim 47 wherein said dilating catheter distal tip has an outer diameter larger than the outer diameter of said distal segment adjacent said step.

* * * * *